United States Patent
Murakami et al.

(10) Patent No.: US 11,891,443 B2
(45) Date of Patent: Feb. 6, 2024

(54) CADM1 V9-RECOGNIZING ANTIBODY

(71) Applicant: The University of Tokyo, Tokyo (JP)

(72) Inventors: Yoshinori Murakami, Tokyo (JP); Takeshi Ito, Tokyo (JP); Takao Hamakubo, Tokyo (JP); Hiroko Iwanari, Tokyo (JP)

(73) Assignee: The University of Tokyo, Tokyo (JP)

( * ) Notice: Subject to any disclaimer, the term of this patent is extended or adjusted under 35 U.S.C. 154(b) by 813 days.

(21) Appl. No.: 16/979,442

(22) PCT Filed: Mar. 18, 2019

(86) PCT No.: PCT/JP2019/011201
§ 371 (c)(1),
(2) Date: Nov. 30, 2020

(87) PCT Pub. No.: WO2019/177173
PCT Pub. Date: Sep. 19, 2019

(65) Prior Publication Data
US 2021/0079092 A1    Mar. 18, 2021

(30) Foreign Application Priority Data
Mar. 16, 2018 (JP) ................................ 2018-049435

(51) Int. Cl.
*C07K 16/28* (2006.01)
*G01N 33/574* (2006.01)

(52) U.S. Cl.
CPC ... *C07K 16/2803* (2013.01); *G01N 33/57423* (2013.01); *G01N 33/57492* (2013.01); *C07K 2317/34* (2013.01); *C07K 2317/565* (2013.01)

(58) Field of Classification Search
None
See application file for complete search history.

(56) References Cited

FOREIGN PATENT DOCUMENTS

WO    2010102175    9/2010
WO    2012119989    9/2012

OTHER PUBLICATIONS

Tanabe et al., "Neuronal RA175/SynCAM1 isoforms are processed by tumor necrosis factor-alpha-converting enzyme (TACE)/ADAM17-like proteases", Oct. 17, 2008, pp. 16-21, vol. 444, No. 1, Publisher: Neurosci Lett.

Declerck Paul J. et al., Generation of Monoclonal Antibodies against Autologous Proteins in Gene-inactivated Mice, Apr. 1995, vol. 270, No. 15, p. 8397-8400.

Fukami Takeshi et al., Identification of the Tslc1 gene, a mouse orthologue of the human tumor suppressor TSLC1 gene, Gene, 2002, vol. 295, p. 7-12.

Hrabovska Anna et al., A Novel System for the Efficient Generation of Antibodies Following Immunization of Unique Knockout Mouse Strains, PLoS one, Sep. 2010, vol. 5, p. 1-7.

Kikuchi Shinji, et al., Expression of a splicing variant of the CADM1 specific to small cell lung cancer, Cancer Science, Jun. 2012, vol. 103, No. 6, p. 1051-1057.

Nagara, Y., et al. Tumor suppressor cell adhesion molecule 1 (CADM1) is cleaved by a disintegrin and metalloprotease 10 (ADAM10) and subsequently cleaved by γ-secretase complex, Biochemical and Biophysical Research Communications, vol. 417, Issue 1, 2012, p. 462-467.

Shirakabe K, et al. Mechanistic insights into ectodomain shedding: susceptibility of CADM1 adhesion molecule is determined by alternative splicing and O-glycosylation. Sci Rep. Apr. 10, 2017;7:46174.

*Primary Examiner* — Changhwa J Cheu
(74) *Attorney, Agent, or Firm* — Suzannah K. Sundby, Esq.; Canady + Lortz LLP

(57) ABSTRACT

The present invention provides an antibody recognizing a v9 fragment of the cell adhesion molecule CADM1.

14 Claims, 10 Drawing Sheets
Specification includes a Sequence Listing.

Figure 2
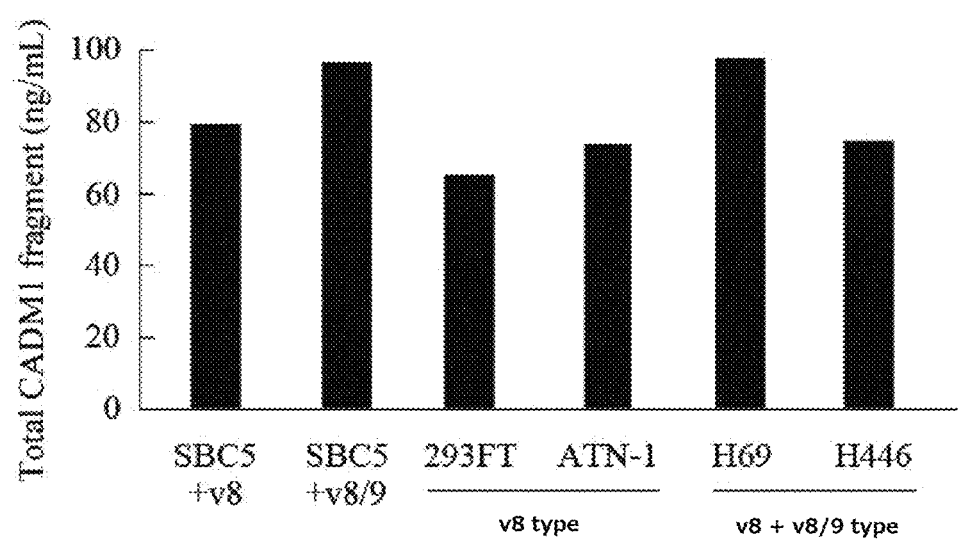
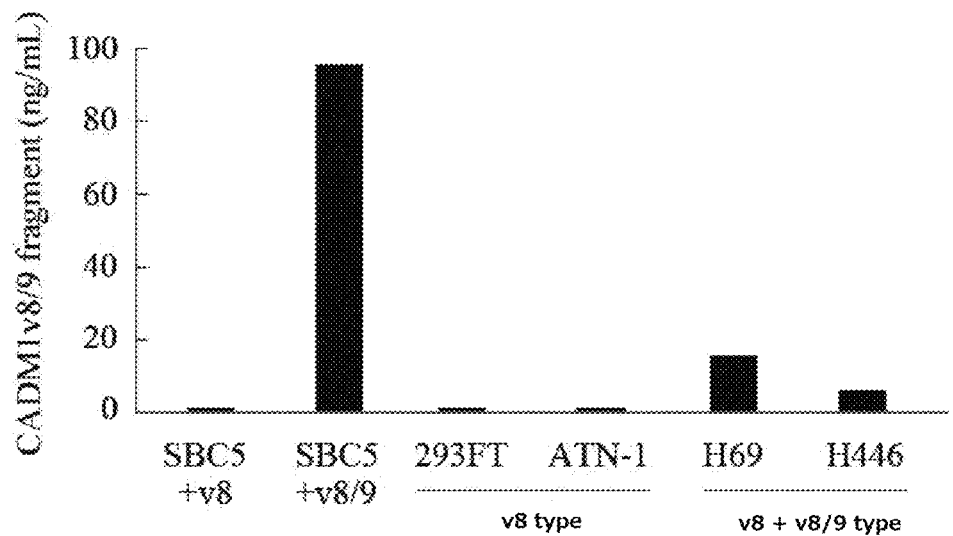

Figure 10

Heavy chain: DNA sequence (423 bp)
Leader sequence-FR1-CDR1-FR2-CDR2-FR3-CDR3-FR4

ATGACATTGAACATGCTGTTGGGGCTGAAGTGGGTTTTCTTTGTTGTTTTTATCAAGGTGTGCATT
GTGAGGTGCAGCTTGTTGAGTCTGGTGGAGGATTGGTGCAGCCTAAAGGGTCATTGAAACTCTCATG
TGCAGCCTCTGGATTCACCTTCAATACCTACGCCATGAACTGGGTCCGCCAGGCTCCAGGAAAGGGT
TTGGAATGGGTTGCTCGCATAAGAAGTAAAAGTAATTATTATACAACATATTATGCCGATTCAGTGA
AAGACAGGTTCACCATCTCCAGAGATGATTCACAAAGCATGCTCTATCTGCAAATGAACAATTTGAA
GACTGAGGACACAGCCATGTATTACTGTATACGACAGAGGCATGGTAACTTCTACTGGGGCCAAGGG
ACTCTGGTCACTGTCTCTGCA

Heavy chain: Amino acids sequence (141 aa)
Leader sequence-FR1-CDR1-FR2-CDR2-FR3-CDR3-FR4

MTLNMLLGLKWVFFVVFYQGVHCEVQLVESGGGLVQPKGSLKLSCAASGFTFNTYAMNWVRQAPGKG
LEWVARIRSKSNYYTTYYADSVKDRFTISRDDSQSMLYLQMNNLKTEDTAMYYCIRQRHGNFYWGQG
TLVTVSA

Light chain: DNA sequence (393 bp)
Leader sequence-FR1-CDR1-FR2-CDR2-FR3-CDR3-FR4

ATGGAGACAGACACAATCCTGCTATGGGTGCTGCTGCTCTGGGTTCCAGGCTCCACTGGTGACATTG
TGCTGACCCAATCTCCAGCTTCTTTGGCTGTGTCTCTAGGGCAGAGGGCCACCATCTCCTGCAAGGC
CAGCCAAAGTGTTGATTATGATGGTTATAGTTATATGAACTGGTACCAACAGAAACCAGGACAGCCA
CCCAAACTCCTCATCTATGCTGCATCCAATCTAGAATCTGGGATCCCAGCCAGGTTTAGTGGCAGTG
GGTCTGGGACAGACTTCACCCTCAACATCCATCCTGTGGAGGAGGAGGATGCTGCAACCTATTACTG
TCAGCAAAGTAATGAGGATCCTCCACGTTCGGAGCTGGGACCAAGCTGGAGCTGAAA

Light chain: Amino acids sequence (131 aa)
Leader sequence-FR1-CDR1-FR2-CDR2-FR3-CDR3-FR4

METDTILLWVLLLWVPGSTGDIVLTQSPASLAVSLGQRATISCKASQSVDYDGYSYMNWYQQKPGQP
PKLLIYAASNLESGIPARFSGSGSGTDFTLNIHPVEEEDAATYYCQQSNEDPPTFGAGTKLELK

Figure 11

▨ Signal sequence

Heavy Chain

MRLLGFLLCLAAALKSVLS

QIQLKESGPA VIEPSQSLSL TCIVSGFSII SSSYCWHWIR QPPGKGLEWM

GRICYEGSIY YSPSIKSRST ISRDTSLNKF FIQLSSVTNE DTAMYYCSRE

RKSTMDYWGQ GTSVTVSS

Light Chain

MMSSAQFLGLLLLCFQGTRC

DIQVTQTTSS LSASLGDRVT ISCRASQDIS NYLNWYQQKP DGTLKLLIYY

TSRLHSGVPS RFSGSGSGTD YSLTISNLDQ EDIATYFCQQ VNALPWTFGG

GTKLEIK

Figure 12

Signal sequence

Heavy Chain

MERHWIFLFLFSVTAGVHS

QVQLQQSGTE LAKPGASVKM SCKASGYTFT HYWMHWVKQR PGQGLEWIGF

INPGTGYTEY NQKFKDKATL TADKSSSTAY IQLSSLTSED SAVYYCSRAS

YYSGSSHAWF GFWGQGTLVT VSA

Light Chain

METDTILLWVLLLWVPGSTG

DIVLTQSPAS LAVSLGQRAT ISCKASQSVN YDGDNYMNWY QQKPGQPPKL

LIYAASNLES GIPARFSGSG SGTDFTLNIH PVEEEDAATY YCQQSYEDPW

TFGGGTKLEI K

CADM1 V9-RECOGNIZING ANTIBODY

REFERENCE TO A SEQUENCE LISTING SUBMITTED VIA EFS-WEB

The content of the ASCII text file of the sequence listing named "20201130_034574_024US1_subseq_ST25" which is 17 kb in size was created on Nov. 20, 2020 and electronically submitted via EFS-Web on Nov. 30, 2020 is incorporated herein by reference in its entirety.

TECHNICAL FIELD

The present invention relates to a CADM1 v9-recognizing antibody.

BACKGROUND ART

Small cell lung cancer (SCLC) accounts for approximately 15% of all lung cancers in Japan, and it is a typical intractable cancer by which 10,000 or more persons die in a year. SCLC exhibits good reactivity to an anticancer agent that is initial chemotherapy. However, the subsequent appearance of an anticancer agent-resistant tumor is inevitable. In addition, SCLC metastasizes to whole body from the early stage thereof, and for such SCLC, there are a few tumor detection markers as sensitive disease state markers. Under such circumstances, the five year survival rate of small cell lung cancer is as low as less than 10%, and thus, it has a poor prognosis.

Since tumor detection markers used to determine the effects of anticancer agents or diagnose reoccurrence are essential for the treatment of SCLC, neuron-specific enolase (NSE) and pro-gastrin-releasing peptide (ProGRP) have been used.

CITATION LIST

Non Patent Literature

Non Patent Literature 1: Kikuchi et al., Cancer Science, 2012, 103(6): 1051-1057
Non Patent Literature 2: Shirakabe et al., Scientific Reports, 2017, 7: 46714
Non Patent Literature 3: Nagara et al., Biochemical and Biophysical Research Communications, 2012, 417(1): 462-467

SUMMARY OF INVENTION

Technical Problem

However, even if the sensitivity is optimized in the method of detecting SCLC, the sensitivity of NSE is approximately 30% or less, and the sensitivity of ProGRP is approximately 45%. Hence, about a half of all small cell lung cancers are undetectable even by using the aforementioned two markers, and thus, these markers become blind spots in the diagnosis and treatment of SCLC. In particular, NSE can never detect tumors in an early stage of SCLC, whereas ProGRP can detect only a few tumors. Therefore, it has been strongly desired to develop a novel tumor marker capable of detecting SCLC that cannot be detected by the existing tumor markers and also capable of detecting an early stage of SCLC.

In view of the foregoing, it is an object of the present invention to provide a novel tumor marker of SCLC.

Solution to Problem

First, the present inventors have conducted intensive studies directed towards achieving the aforementioned object. As a result, the present inventors have found that the cell adhesion molecule CADM1 is highly expressed in SCLC and further, its splice variant v8/9 is expressed almost only in the testis among normal tissues, and that the expression of CADM1 v8/9 promotes the suspension growth of SCLC cells and oncogenicity in mice, while down regulation of CADM1 v8/9 expression suppresses the spheroid forming ability, survival, and growth of SCLC cells (Non Patent Literature 1).

Second, although CADM1 v8/9 is cleaved by ADAM17 and an extracellular region is released as a fragment (Non Patent Literature 2), the amino acid sequence encoded by exon 9 that is characterized for CADM1 v8/9 is located outside and just adjacent to the cell membrane and is included in the released fragment. On the other hand, in normal tissues other than the testis, for example, in epithelial cells, CADM1 is cleaved by ADAM10, and an extracellular region is released as a fragment (Non Patent Literature 3). However, since CADM1 v8/9 is not expressed at all therein, the amino acid sequence encoded by exon 9 that is characterized for CADM1 v8/9 is not located outside and just adjacent to the cell membrane and is not included in the released fragment, either. Moreover, a CADM1 v9 fragment that can be released from the testis hardly transfers into blood stream and the like. Thus, the present inventors have found that the v9 fragment of CADM1 is promising as a specific molecular target in the diagnosis of SCLC.

However, it has been extremely difficult to produce an anti-CADM1 antibody using mammals. A human CADM1 protein has high homology to the CADM1 protein of a mammal as an experimental animal (a mouse, a rabbit, etc.), and further, CADM1 fragments are also present in the blood of a normal individual. Accordingly, even though such a mammalian experimental animal was immunized with a human CADM1 protein, no antibodies could be obtained. Therefore, it has been considered for many years that it is difficult to produce an antibody that specifically recognizes the v9 fragment of CADM1.

The present inventors have backcrossed CADM1 gene knockout mice to Balb/c line over 2 or more years to prepare mice. Then, the inventors have found that the prepared mice are immunized by the v9 fragment of CADM1, so that antibodies specific to the v9 fragment of CADM1 can be produced, thereby completing the present invention.

Specifically, the present invention is as follows.

[1]
An antibody recognizing a v9 fragment of CADM1.
[2]
The antibody according to the above [1], wherein the v9 fragment of CADM1 is a v9 fragment of human CADM1.
[3]
The antibody according to the above [1] or [2], wherein the antibody recognizes an amino acid sequence DTTATTEPAVH of CADM1 as set forth in SEQ ID NO: 2 derived from exon 9.
[4]
An antibody comprising:
a heavy chain CDR1 consisting of an amino acid sequence as set forth in SEQ ID NO: 3, a heavy chain CDR2 consisting of an amino acid sequence as set forth in SEQ ID NO: 4, a heavy chain CDR3 consisting of an amino acid sequence as set forth in SEQ ID NO: 5, a light chain CDR1 consisting of an amino acid sequence as set forth in SEQ ID NO: 6, a light chain CDR2 consisting of an amino acid sequence as set forth in SEQ ID NO: 7, and a light chain CDR3 consisting of an amino acid sequence as set forth in SEQ ID NO: 8.

[5]

An antibody comprising:

a heavy chain comprising an amino acid sequence as set forth in SEQ ID NO: 9, and a light chain comprising an amino acid sequence as set forth in SEQ ID NO: 10.

[6]

A tumor detection marker comprising the antibody according to any of the above [1] to [5].

[7]

The tumor detection marker according to the above [6], for use in detection of a tumor associated with the v9 fragment of CADM1.

[8]

The tumor detection marker according to the above [6] or [7], wherein the tumor associated with the v9 fragment of CADM1 is small cell lung cancer.

[9]

The tumor detection marker according to any of the above [6] to [8], wherein any of serum, plasma and pleural effusion is used as a biological sample.

[10]

A tumor detection kit, comprising the antibody according to any of the above [1] to [5] or the tumor detection marker according to any of the above [6] to [9].

[11]

The tumor detection kit according to the above [10], wherein the antibody or the tumor detection marker is used in any of an ELISA method, a CLEIA method, a fluorescent antibody method, an enzyme antibody method, a Western blotting method, and an immunoprecipitation method.

[12]

A tumor detection method of detecting a tumor using the antibody according to any of the above [1] to [5], the tumor detection marker according to any of the above [6] to [9], or the tumor detection kit according to the above [10] or [11].

Advantageous Effect of Invention

According to the present invention, a novel tumor marker of SCLC can be provided.

BRIEF DESCRIPTION OF DRAWINGS

FIG. 2 shows the detection results of the v9 fragment of CADM1 in a cell culture supernatant.

FIG. 10 shows the amino acid sequences and nucleotide sequences of the heavy chain and light chain of the antibody F1222. The sequences from top to bottom are SEQ ID NO: 37, SEQ ID NO: 9, SEQ ID NO: 42, and SEQ ID NO: 38.

FIG. 11 shows the amino acid sequences of the heavy chain (SEQ ID NO: 17) and light chain (SEQ ID NO: 18) of the antibody E9919.

FIG. 12 shows the amino acid sequences of the heavy chain (SEQ ID NO: 25) and light chain (SEQ ID NO: 26) of the antibody E9935.

DESCRIPTION OF EMBODIMENTS

Figure 1:
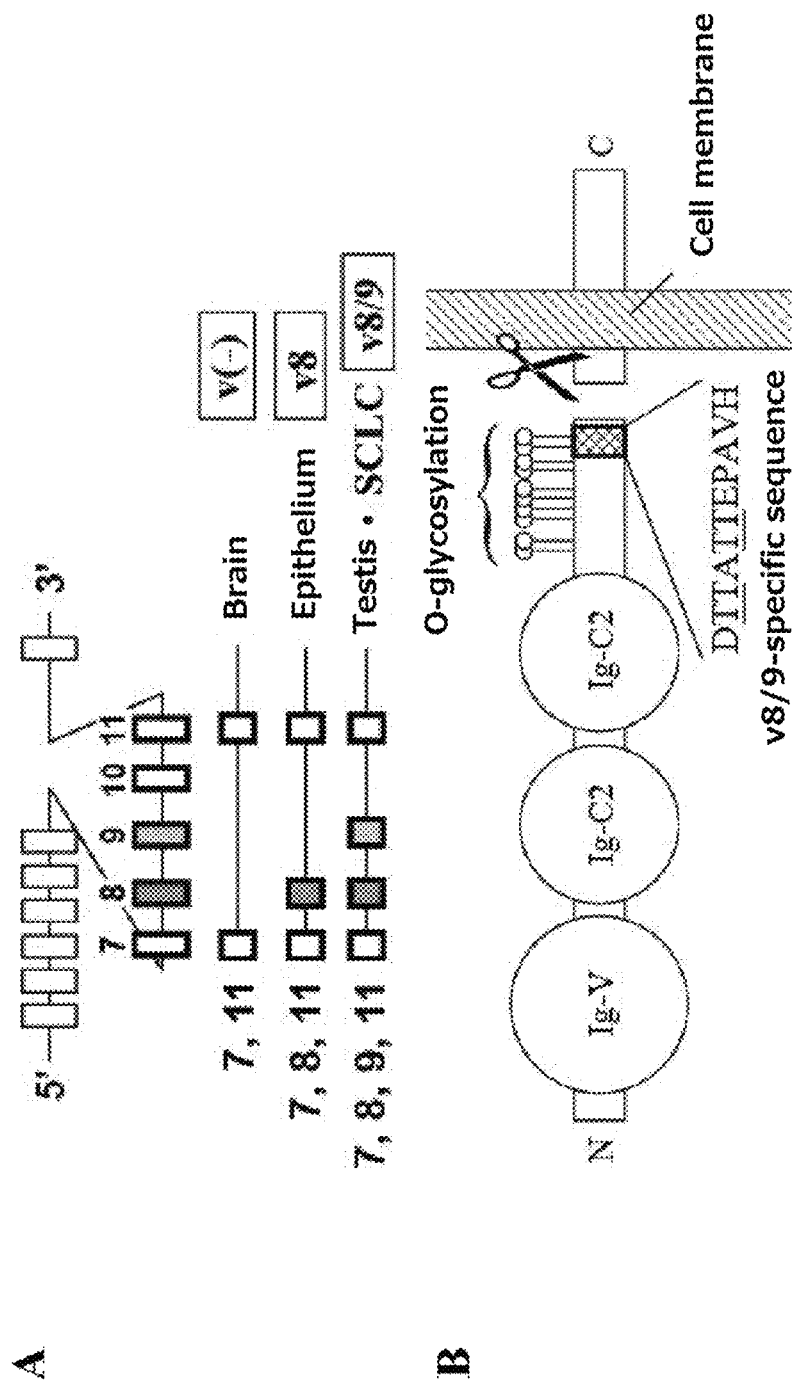
FIG. 1 is a schematic view showing the structures of the mRNA and protein of the splice variant v8/9 of CADM1. The V8/9-specific sequence is SEQ ID NO: 1.

The present invention will be specifically described in the embodiments for carrying out the present invention. However, the present invention is not limited to the following embodiments for carrying out the present invention and can be carried out in various modifications.

The contents as disclosed in the publications referenced in the present invention are incorporated in the present invention by reference.

[CADM1 v9-Recognizing Antibody]

It has been considered in many years that it is difficult to produce an antibody specific to the v9 fragment of CADM1. The antibody according to the present invention recognizes the v9 fragment of CADM1. In particular, the antibody according to the present invention can recognize the v9 fragment of CADM1 that is the extracellular domain of CADM1, which is cleaved by protease (ADAM10 or ADAM17) and is released. In this context, "the v9 fragment of CADM1" means the extracellular region of the cell adhesion molecule CADM1, in which CADM1 v8/9 comprising the domain corresponding to exon 9 (SEQ ID NO: 1) is cleaved by protease, etc., and is released as a fragment from the cells. On the other hand, "CADM1 v8/9" means the splice variant v8/9, which is expressed by the cell adhesion molecule CADM1 in tumors and in the testis in normal tissues. The antibody according to the present invention is also referred to as "CADM1 v9-recognizing antibody," "v9-recognizing antibody," "anti-CADM1 v9 antibody," or "anti-v9 antibody." On the other hand, "the v9 fragment of CADM1" is also referred to as "CADM1 v9 fragment" or "v9 fragment," as well as "the v9 fragment of CADM1."

The CADM1 v9-recognizing antibody is used in detection of a tumor associated with the v9 fragment of CADM1 (hereinafter also referred to as a "v9 fragment-associated tumor"). In this context, the "tumor associated with the v9 fragment of CADM1" means tumor tissues that release the v9 fragment. In the case of SCLC, CADM1 v8/9, which is expressed almost exclusively in the testis in normal tissues, is expressed in tumor tissues, and such CADM1 v8/9 is not expressed in tissues other than the testis. Thus, by using a CADM1 v9-recognizing antibody, the v9 fragment of CADM1 can be specifically recognized, and tumor tissues can be detected. In this context, the phrase "specifically recognize the v9 fragment of CADM1" means that the CADM1 v9-recognizing antibody recognizes the v9 fragment of CADM1 more strongly than the fragment of CADM1 that does not comprise a region corresponding to exon 9, in the extracellular region of the cell adhesion molecule CADM1.

By using the CADM1 v9-recognizing antibody, the presence of tumor tissues can be detected with higher specificity and higher sensitivity than the use of conventional antibodies. Therefore, the CADM1 v9-recognizing antibody can be more effectively used in the screening of a subject who is suspected of being infected with cancer including small cell lung cancer and the monitoring of the tumor recurrence of a patient who is diagnosed to have cancer. For example, as shown in the after-mentioned Examples, by using the CADM1 v9-recognizing antibody, tumor tissues can be detected with high specificity and high sensitivity even in a patient with limited-stage SCLC that is the SCLC at an early stage (wherein the lesion is limited to ipsilateral thorax, contralateral mediastinum, and contralateral supraclavicular lymph node and does not have malignant pleural effusion and pericardial effusion).

Specifically, the CADM1 v9-recognizing antibody recognizes at least one amino acid sequence of the following amino acid sequences:
(1) the amino acid sequence DTTATTEPAVH of CADM1 as set forth in SEQ ID NO: 2 derived from exon 9;
(2) an amino acid sequence having a deletion, substitution, or addition of one or more amino acids in the amino acid sequence DTTATTEPAVH of CADM1 as set forth in SEQ ID NO: 2 derived from exon 9; and
(3) an amino acid sequence having identity of 90% or more, preferably 95% or more, and more preferably 98% or more to the amino acid sequence DTTATTEPAVH of CADM1 as set forth in SEQ ID NO: 2 derived from exon 9.

The site recognized by the CADM1 v9-recognizing antibody is not particularly limited, as long as it is a region corresponding to exon 9 in the v9 fragment of CADM1. For example, the v9 fragment of CADM1 recognized by the CADM1 v9-recognizing antibody is the v9 fragment of human CADM1 shown in the Examples, and in particular, a region thereof corresponding to exon 9 thereof.

In the present description, the term "amino acid" is used in the broadest sense, and the "amino acid" means to include not only natural amino acids, but also non-natural amino acids such as amino acid variants and derivatives. Examples of the amino acid include, but are not limited to: natural proteinogenic L-amino acids; D-amino acids; chemically modified amino acids such as amino acid variants and derivatives; natural non-proteinogenic amino acids such as norleucine, β-alanine, or ornithine; and chemically synthesized compounds having properties known in the present technical field, which are the characteristics of amino acids. Examples of the non-natural amino acids include, but are not limited to: α-methylamino acids (α-methylalanine, etc.), D-amino acids, histidine-like amino acid (2-amino-histidine, β-hydroxy-histidine, homohistidine, α-fluoromethyl-histidine, α-methyl-histidine, etc.), amino acids having residual methylene on the side chain ("homo" amino acids), and amino acids in which the carboxylic acid functional group in the side chain is replaced with a sulfonic acid group (cysteic acid, etc.).

In the present description, in the case of using the phrase "have a deletion, substitution, or addition of one or more amino acids," the number of amino acids to be deleted, substituted or otherwise is not particularly limited, as long as the resulting set of CDRs retains antigen recognition function. In addition, the term "more" herein means an integer of 2 or more, preferably several, for example, 2 to 5, and more preferably 2, 3, or 4. The position of deletion, substitution or addition in each CDR may be the N-terminus or C-terminus of each CDR, or an intermediate position thereof, as long as the resulting set of CDRs retains antigen recognition function.

In the present description, the phrase "have identity of Y % or more to the amino acid sequence as set forth in SEQ ID NO: X" means that when the amino acid sequences of two polypeptides are aligned (alignment) so that the matching of the two amino acid sequences becomes maximum, the percentage of the number of amino acid residues that are common in the two sequences to the total number of amino acids shown in SEQ ID NO: X is Y % or more.

The CADM1 v9-recognizing antibody may be either a monoclonal antibody or a polyclonal antibody. In addition, the antibody according to the present invention may be any isotype of IgG, IgM, IgA, IgD, and IgE.

The CADM1 v9-recognizing antibody may be a mouse antibody, a human CDR-grafted antibody, a human chimeric antibody, a humanized antibody, or a complete human antibody, or may also be a low-molecular-weight antibody, as long as it recognizes the v9 fragment of CADM1 released from the cells. However, the CADM1 v9-recognizing antibody is not limited to these antibodies.

The human CDR-grafted antibody is an antibody, in which the CDR of the antibody of an animal other than a human is substituted with the CDR of a human antibody. The human chimeric antibody is an antibody consisting of a variable region derived from the antibody of an animal other than a human and a constant region derived from a human antibody. The humanized antibody is the antibody of an animal other than a human, into which a human antibody-derived portion is incorporated, while some region with high safety of the other animal antibody remains. The concept of the humanized antibody includes a human chimeric antibody and a human CDR-grafted antibody.

In the present description, the "low-molecular-weight antibody" means an antibody fragment, or an antibody fragment to which any given molecule binds, wherein the antibody fragment recognizes the same epitope which the original antibody recognizes. Specific examples of the low-molecular-weight antibody include, but are not limited to: Fab consisting of VL, VH, CL, and CH1 regions; F(ab')2, in which two Fab fragments are linked to each other via a disulfide bond in a hinge region; Fv consisting of VL and VH; scFv that is a single chain antibody, in which VL and VH are linked to each other via an artificial polypeptide linker; sdFv; Diabody; and sc(Fv)2.

The CADM1 v9-recognizing antibody is not particularly limited, and examples thereof include an antibody comprising: (a) heavy chain CDR1 consisting of the amino acid sequence as set forth in SEQ ID NO: 3, (b) heavy chain CDR2 consisting of the amino acid sequence as set forth in SEQ ID NO: 4, (c) heavy chain CDR3 consisting of the amino acid sequence as set forth in SEQ ID NO: 5, (d) light chain CDR1 consisting of the amino acid sequence as set forth in SEQ ID NO: 6, (e) light chain CDR2 consisting of the amino acid sequence as set forth in SEQ ID NO: 7, and (f) light chain CDR3 consisting of the amino acid sequence as set forth in SEQ ID NO: 8.

Examples of the CADM1 v9-recognizing antibody also include any of the following antibodies:

(1) an antibody comprising, a heavy chain comprising the amino acid sequence as set forth in SEQ ID NO: 9, and a light chain comprising the amino acid sequence as set forth in SEQ ID NO: 10;

(2) an antibody comprising, a heavy chain comprising the amino acid sequence as set forth in SEQ ID NO: 9 or an amino acid sequence having a deletion, substitution, or addition of one or more amino acids in the aforementioned amino acid sequence, and a light chain comprising the amino acid sequence as set forth in SEQ ID NO: 10 or an amino acid sequence having a deletion, substitution, or addition of one or more amino acids in the aforementioned amino acid sequence; and (3) an antibody, comprising a heavy chain comprising an amino acid sequence having identity of 90% or more, preferably 95% or more, and more preferably 98% or more to the amino acid sequence as set forth in SEQ ID NO: 9, and a light chain comprising an amino acid sequence having identity of 90% or more, preferably 95% or more, and more preferably 98% or more to the amino acid sequence as set forth in SEQ ID NO: 10.

[Method of Producing CADM1 v9-Recognizing Antibody]

The method of producing the CADM1 v9-recognizing antibody is not limited. For example, when the CADM1 v9-recognizing antibody is a monoclonal antibody, antibody-producing cells are isolated from a non-human mammal immunized with the v9 fragment of CADM1 and are then fused with myeloma cells, etc. to produce hybridomas. An antibody produced by these hybridomas is purified, so that the CADM1 v9-recognizing antibody can be obtained. On the other hand, when the CADM1 v9-recognizing antibody is a polyclonal antibody, the antibody can be obtained from the serum of an animal immunized with the v9 fragment of CADM1. The v9 fragment of CADM1 used in the immunization is not particularly limited, as long as it is recognized by the obtained antibody.

Commercially available CADM1 monoclonal antibodies for practical use are only avian antibodies (avian anti-human CADM1 antibodies) (see Non Patent Literature 2), and these antibodies cannot recognize the v9 fragment of CADM1, regardless of whether the antibodies are avian antibodies or mammalian antibodies. Although researches over the world had challenged to produce a mammalian antibody capable of recognizing the v9 fragment of CADM1, no successful examples had been reported so far. As described in the Examples later, the present inventors have conducted studies for a long period of time, and specifically, the inventors have backcrossed Cadm1$^{-/-}$ mice to Balb/c line for 2 years to obtain Balb/c, Cadm1$^{-/-}$ mice. The obtained Balb/c, Cadm1$^{-/-}$ mice have been immunized with the CADM1 v9 fragment, so that a mammalian antibody capable of recognizing the v9 fragment of CADM1 has been obtained for the first time.

In the case of producing an antibody having a specific amino acid sequence, for example, a suitable host is transformed with an expression vector comprising a nucleic acid encoding the antibody, and the transformant is then cultured under suitable conditions, so that it is allowed to express the antibody, and thereafter, the antibody is isolated and purified according to a known method, so as to produce the antibody. Examples of the isolation and purification method include an affinity column using protein A, etc., other chromatography columns, filters, ultrafiltration, salting-out, and dialysis. These methods can be used in combination, as appropriate.

In addition, the "antibody Y specifically binding to the same epitope to which certain antibody X binds" can be produced after the sequence of the epitope has been determined, as described below.

For example, a large number of peptides having random sequences are immobilized on a solid-phase carrier, arrayed, and reacted with the antibody X. Thereafter, the bonds are detected using an enzyme-labeled secondary antibody, the amino acid sequence of a peptide, to which the antibody X specifically binds, is examined. The homology of this amino acid sequence to the amino acid sequence of an antigenic protein is searched, so that the epitope on the antigenic protein can be determined. The peptides immobilized on the solid-phase carrier may have previously been determined to be a partial peptide group of the antigenic protein. Otherwise, the binding of the antibody X to the antigenic protein is detected according to an ELISA method, in the presence of various partial peptides of the antigenic protein, and the presence or absence of competitive activity is examined, so that the epitope on the antigenic protein can be determined.

If the sequence of the epitope can be determined, the antibody Y specifically binding to the epitope can be produced by a person skilled in the art according to a known method. For instance, a peptide comprising the epitope sequence is immobilized on a solid-phase carrier, and the binding of the peptide to various antibodies is detected, so that an antibody specifically binding to the epitope can be obtained.

As "various antibodies" used herein, an antibody obtained by immunizing an animal with an antigenic protein or a partial peptide thereof may be used, or an antibody library or an antibody fragment library that are produced according to a phage display method may also be used. In the case of using a library produced according to such a phage display method, a peptide comprising an epitope sequence is immobilized on a solid-phase carrier, and panning is repeated, so that the antibody Y specifically binding to the epitope can be obtained.

The human chimeric antibody and the human CDR-grafted antibody can be each produced by cloning an antibody gene from the mRNA of hybridomas producing the antibody of an animal other than a human, and ligating the antibody gene to a part of a human antibody gene according to a gene recombination technique.

For example, in the case of the human chimeric antibody, cDNA is synthesized from the mRNA of hybridomas producing a mouse antibody using reverse transferase, and the heavy chain variable region (VH) and the light chain variable region (LH) are cloned according to PCR, followed by sequencing. Subsequently, a 5'-primer comprising a leader sequence is produced from the nucleotide sequence of an antibody having a high matching rate, and using the 5'-primer and the variable region 3'-primer, a region ranging from the signal sequence to the 3'-terminus of the variable region in the above-described cDNA is cloned according to PCR. On the other hand, the heavy chain and light chain constant regions of human IgG1 are cloned, and regarding each of the heavy chain and the light chain, the mouse antibody-derived variable region is ligated to the human antibody-derived constant region by an overlapping hanging method based on PCR, followed by amplification. The obtained DNA is inserted into a suitable vector and is then used in transformation to obtain a human chimeric antibody.

In the case of the CDR-grafted antibody, a human antibody variable region having the highest homology to a mouse antibody variable region used is selected and cloned, and the nucleotide sequence of CDR is modified by performing site-directed mutagenesis involving a mega-primer method. Besides, if the specific binding to an antigen becomes impossible by humanization of the amino acid sequence constituting the framework region, the amino acids of a part of the framework may be changed from the human sequence to the rat sequence.

Examples of other methods of producing antibodies include: an Adlib method, in which an antibody-producing cell line is obtained from a trichostatin A-treated chicken B cell-derived DT40 cell line (Seo, H. et al., Nat. Biotechnol., 6: 731-736, 2002); and a method of producing a human antibody, comprising immunization of a KM mouse, into which a human antibody gene is introduced while the mouse antibody gene is destructed (Itoh, K. et al., Jpn. J. Cancer Res., 92: 1313-1321, 2001; Koide, A. et al., J. Mol. Biol., 284: 1141-1151, 1998). These methods can also be applied to production of the CADM1 v9-recognizing antibody.

When the CADM1 v9-recognizing antibody is a low-molecular-weight antibody, the antibody may be expressed according to the above-described method, using DNA encoding the low-molecular-weight antibody, or the antibody may also be produced by treating the full-length antibody with an enzyme such as papain or pepsin.

The CADM1 v9-recognizing antibodies may be different in terms of amino acid sequence, molecular weight, isoelectric point, the presence or absence of a sugar chain, form, and the like, depending on the production method or purification method thereof. However, as long as the obtained antibody has function equivalent to that of the CADM1 v9-recognizing antibody, the antibody is included in the present invention. For example, when the CADM1 v9-recognizing antibody is expressed in prokaryotic cells such as *Escherichia coli*, a methionine residue is added to the N-terminus of the amino acid sequence of the original antibody. Such an antibody is also included in the present invention.

[Tumor Detection Marker]

The tumor detection marker according to the present invention comprises the CADM1 v9-recognizing antibody and may further comprise carriers or additives. Examples of such carriers and additives include, but are not limited to, pharmaceutically acceptable organic solvents such as water, a saline, a phosphate buffer, dextrose, glycerol, or ethanol, collagen, polyvinyl alcohol, polyvinyl pyrrolidone, a carboxy vinyl polymer, carboxymethyl cellulose sodium, sodium polyacrylate, sodium alginate, water-soluble dextran, carboxymethyl starch sodium, pectin, methyl cellulose, ethyl cellulose, xanthan gum, gum Arabic, casein, agar, polyethylene glycol, diglycerin, glycerin, propylene glycol, Vaseline, paraffine, stearyl alcohol, stearic acid, human serum albumin, mannitol, sorbitol, lactose, and a surfactant.

The tumor detection marker according to the present invention comprises the CADM1 v9-recognizing antibody, so that it can detect the v9 fragment of CADM1, which cannot be recognized by conventional markers such as NSE or ProGRP. Moreover, since the tumor detection marker according to the present invention can detect the v9 fragment of CADM1, detection rates in detection of tumors, such as sensitivity and specificity, can be improved. That is to say, among tumors, in particular, an early stage of SCLC tumor can never be detected by NSE and can be hardly detected by ProGRP, which are both conventional representative markers. In contrast, by using the tumor detection marker according to the present invention, the detection rates of tumors can be improved.

[Tumor Detection Kit]

The tumor detection kit according to the present invention comprises the CADM1 v9-recognizing antibody or the tumor detection marker. The intended use of the present tumor detection kit is not particularly limited, and the present tumor detection kit is used in detection of the v9 fragment of CADM1, or detection of a tumor associated with the v9 fragment of CADM1.

The tumor detection kit may also comprise carriers or additives, as well as the reagent and the tumor detection marker, depending on the intended use thereof. The tumor detection kit may further comprise a buffer, a container, an instruction manual, and the like.

The CADM1 v9-recognizing antibody, and the tumor detection marker and kit are used in detection of tumors associated with the v9 fragment of CADM1 (v9 fragment-associated tumors), and in particular, detection of cancers. They are used in detection of, among other cancers, neurogenic tumors such as neuroendocrine tumor and neuroblastoma, the detection being based on the release of the v9 fragment of CADM1 from the cells. The neuroendocrine tumor is not particularly limited, as long as it is a tumor generated from neuroendocrine cells (hormone-producing cells). The neuroendocrine tumor can be generated in neuroendocrine cells in the lung (lung carcinoid and lung large-cell neuroendocrine carcinoma), pancreas, digestive tract, thyroid gland, etc. Examples of the tumor generated in the lung include small cell lung cancer (SCLC), lung carcinoid, and lung large-cell neuroendocrine carcinoma. The CADM1 v9-recognizing antibody, and the tumor detection marker and kit are particularly preferably used in detection of small cell lung cancer (SCLC). Since the CADM1 v9-recognizing antibody is excellent in specificity and sensitivity of tumor detection, it can be preferably utilized in detection of SCLC.

[Tumor Detection Method]

In the tumor detection method according to the present invention, a tumor is detected using the CADM1 v9-recognizing antibody, the tumor detection marker, or the tumor detection kit. The detection method is not particularly limited, as long as it is a detection method using an antibody. For instance, the CADM1 v9-recognizing antibody, the tumor detection marker, or the tumor detection kit is used in any of an ELISA (Enzyme-Linked ImmunoSorbent Assay) method, a CLEIA (chemiluminescent enzyme immunoassay) method, a fluorescent antibody method, an immunoassay antibody method, a Western blotting method, and an immunoprecipitation method, so that a tumor can be detected.

With regard to the tumor detection method according to the present invention, if a sandwich ELISA method is taken as a specific example among ELISA methods, the sandwich ELISA method comprises a step of adsorbing a capture antibody against a sample derived from a subject on a solid phase, a step of blocking the solid phase with skim milk or the like, and a step of adding the subject-derived sample and a CADM1 v9-recognizing antibody to the solid phase. The sandwich ELISA method may further comprise a step of washing away an unreacted portion of the subject-derived sample and an unreacted portion of the CADM1 v9-recognizing antibody. A more particular example of the sandwich ELISA method is one presented in the Examples.

In the present description, the "subject-derived sample" means a sample that may comprise the v9 fragment of CADM1 released from cells. Specific examples of the subject-derived sample include serum, plasma, pleural effusion, urine, sputum, peritoneal fluid, bladder-washed fluid, secretion (e.g., breast secretion), mouth-washed fluid, and aspirate. Among these samples, serum, plasma, and pleural effusion are preferable because these are superior in specificity and sensitivity of the detection of a tumor.

The tumor detection method according to the present invention is a method of promptly detecting a tumor, with high specificity and high sensitivity. This method can be used, for example, in the screening of a subject who is suspected of being infected with cancer including small cell lung cancer and the monitoring of the tumor recurrence of a patient who is diagnosed to have cancer.

[Therapeutic Agent or Preventive Agent]

The therapeutic agent or preventive agent according to the present invention comprises the CADM1 v9-recognizing antibody and may further comprise the same carriers or additives as those used in the aforementioned tumor detection marker.

[Therapeutic Method]

The therapeutic method or preventive method according to the present invention treats or prevents a tumor, using the CADM1 v9-recognizing antibody.

EXAMPLES

Hereinafter, the present invention will be specifically described by the following Examples. However, the present invention is not limited to the following Examples.

<Materials and Methods>

Mice and Cells

Wild-type Balb/c mice were purchased from CLEA Japan, Inc. Cadm1 knockout mice (Cadm1$^{-/-}$) were produced according to a known method (Yamada D et al., Mol Cell Biol, 2006) and were backcrossed to Balb/c mice 10 times. The gp64-tg (transgenic) mice of the Balb/c line were produced according to a known method (Saitoh R et al., J Immunol Methods, 2007). These mice were crossed to each other to produce Cadm1$^{-/-}$/gp64-tg mice of the Balb/c line.

SBC5 cells were purchased from JCRB Cell Bank, 293FT cells were purchased from Thermo Fisher Scientific, ATN-1 cells were purchased from RIKEN BioResource Research Center, and NCI-H69 and NCI-H446 cells were purchased from American Type Culture Collection. Each of the following media was supplemented with 10% FBS (BioWest), 100 units/mL penicillin, and 100 mg/mL streptomycin (Sigma-Aldrich), and the SBC5 cells were cultured in EMEM (Wako Pure Chemical Industries, Ltd.), the 293FT cells were cultured in DMEM (NACALAI TESQUE, INC.), and the ATN-1, NCI-H69, and NCI-H446 cells were cultured in RPMI1640 (NACALAI TESQUE, INC.). The SBC5 cell lines, in which CADM1 v8 (exon 7+8+11 type) and CADM1 v8/9 (exon 7+8+9+11 type) were stably expressed, were obtained by cloning each cDNA into the SalI site of a pBactSTneo vector (furnished from Institute of Physical and Chemical Research, Japan (RIKEN)), transiently transfecting the cells using Lipofectamine LTX (Invitrogen), and then selecting the cells with 500 mg/mL G418 (NACALAI TESQUE, INC.).

Production of Anti-CADM1 Monoclonal Antibody

The anti-CADM1 antibodies E9919 (SEQ ID NOS: 11 to 18) and E9935 (SEQ ID NOS: 19 to 26) were produced as follows.

Cadm1$^{-/-}$/gp64-tg mice of the Balb/c line were used as immune animals. A baculovirus expressing CADM1 v8/9 was used as an antigen. The cDNA of CADM1 v8/9 was cloned into pBlueBac4.5 (Invitrogen), and a recombinant baculovirus was then produced according to a known method (Masuda K et al., J Biol Chem, 2003). Hybridomas were obtained by fusing antibody-producing cells obtained from the spleen excised after the immunization with mouse myeloma-derived SP2/0 cells according to cell fusion. Hybridoma clones producing antibodies specifically recognizing CADM1 in a culture supernatant were evaluated according to an ELISA method for reactivity to CADM1 EC-Fc (Murakami S et al., PLoS One, 2014) in which the Fc region of mouse IgG was added to the C-terminal side of the extracellular region of CADM1, and were then selected.

Production of Anti-CADM1 v9 Antibody

The anti-CADM1 v9 antibodies F1222 (SEQ ID NOS: 3 to 10 and 31 to 38) and F1315 were produced as follows.

Cadm1$^{-/-}$ mice of the Balb/c line were used as animals to be immunized. The peptide CDTTATTEPAVHD (SEQ ID NO: 2) comprising 12 amino acids from the C-terminus of the CADM1 v8/9 fragment, to the cysteine residue of which KLH was added, was used as an antigen. The synthesis of the peptide and addition of KLH thereto were outsourced to ProteinPurify Co. LTD. Immunization was carried out by injecting the antigen into the abdominal cavity, and hybridomas were obtained by fusing the splenic cells with mouse myeloma-derived SP2/0 cells according to cell fusion. For selection of clones producing antibodies recognizing the CADM1 v9 fragment, the clones were evaluated according to an ELISA method for reactivity to CADM1 v8/9 fragment proteins purified from a culture supernatant of the SBC5 cell line stably expressing CADM1 v8/9, and were then selected.

Purification of CADM1 v9 Fragment

A purified protein including CADM1 v9 fragment was obtained by the following method. The SBC5 cell line stably expressing CADM1 v8/9 was cultured in a 15 cm dish (TPP), and when the cells became semi-confluent, the medium was exchanged with a serum-free medium. The cells were culture overnight, and the supernatant was recovered. Subsequently, Protein A Sepharose (Thermo Fisher Scientific) was crosslinked to the anti-CADM1 antibody E9935. Protein A was mixed with E9935, and the mixture was reacted overnight at 4° C. Thereafter, the reaction mixture was reacted with 40 mM DMP (Thermo Fisher Scientific) dissolved in 0.15 M sodium borate (MP biomedicals) at room temperature for 30 minutes for crosslinking. The crosslinked mixture was reacted with 0.2 M Glycine (pH 8) at room temperature for 2 hours to terminate the crosslinking, and the resultant was washed with PBS. To the culture supernatant, the E9935-crosslinked Protein A Sepharose was added, and the obtained mixture was reacted overnight at 4° C. The reaction mixture was washed with PBS four times, and 0.1 M Glycine (pH 2) was then added to the Protein A Sepharose. The obtained mixture was reacted on ice for 1 hour to elute a CADM1 v9 fragment, and 1 M Tris-HCl (pH 9) was added for neutralization. The yield and purity of the obtained CADM1 v9 fragment were confirmed by subjecting the CADM1 v9 fragment to polyacrylamide electrophoresis, and then performing silver staining on the resultant, using Silver Stain MS Kit (Wako Pure Chemical Industries, Ltd.).

Protocols of Sandwich ELISA

Detection of the CADM1 v9 fragment was carried out by a sandwich ELISA method. The anti-CADM1 antibody E9935 was used as a capture antibody. Regarding detection antibodies, for detection of the CADM1 v8/9 fragment, the anti-CADM1 v9 antibody F1222 was used, and the anti-CADM1 antibody E9919 was used for detection of all of CADM1 fragments. Such detection antibodies were HRP-labeled using Peroxidase Labeling Kit-NH$_2$ (DOJINDO LABORATORIES).

First, 100 mL of the capture antibody diluted in a carbonate buffer (15 mM Na$_2$CO$_3$, 35 mM NaHCO$_3$, and 0.2% NaN$_3$) to a concentration of 1 mg/mL was added to Nunc MaxiSorp 96-well plate (Thermo Fisher Scientific) and was left at rest at 4° C. overnight for immobilization. PBS-T (137 mM NaCl, 8.1 mM $Na_2PO_4$, 2.68 mM KCl, 1.47 mM $KH_2PO_4$, and 0.05% Tween 20) was used for washing twice, and 200 mL of 1%/BSA (Wako Pure Chemical Industries, Ltd.)/PBS-T was added. The plate was left at rest at room temperature for 1 hour for blocking. The plate was washed with PBS-T twice, and thereafter, a standard for a calibration curve, a culture supernatant, and serum or pleural effusion were added, followed by incubation at room temperature for 1 hour. The plate was washed with PBS-T four times, and 100 mL of the detection antibody diluted in 1% BSA/PBS-T to a concentration of 100 ng/mL was added, followed by incubation at room temperature for 1 hour. The plate was washed with PBS-T six times, and 100 mL of TMB Soluble Reagent (ScyTek Laboratories) was then added for color development. 100 mL of TMB Stop Buffer (ScyTek Laboratories) was further added to terminate the reaction. Finally, using an Ensight plate reader (PerkinElmer), the wavelength at 450 nm was measured.

As the standard for a calibration curve, a CADM1 v9 fragment protein purified from the culture supernatant of the SBC5 cell line stably expressing CADM1 v8/9 was used. In the case of measuring the CADM1 v9 fragment in serum, the value of Normal Human Serum (Jackson ImmunoResearch Laboratories) was corrected to be 0.

Obtaining of Serum and Pleural Effusion

The blood and pleural effusion of a certain patient were used as research materials. When blood sampling from the certain patient was determined to be necessary for diagnosis and/or treatment and the patient was subjected to a blood sampling test, 10 mL of blood to be used in the present research was also sampled. When a pleural effusion puncture test was carried out, 10 mL of pleural effusion was utilized for the present research, from the total pleural effusion sampled by clinical decision. The blood and/or pleural effusion was centrifuged, and cell components were removed. In the case of blood, serum was used as a research material.

Method of Determining Epitope of Anti-CADM1 v9 Antibody

The anti-CADM1 v9 antibodies F1222 and F1315 were previously HRP-labeled using Peroxidase Labeling Kit-$NH_2$ (DOJINDO LABORATORIES), and epitopes were narrowed down according to an ELISA method. Peptide synthesis was outsourced to Toray Research Center, Inc. The peptide was dissolved in 10% DMSO/PBS to prepare a peptide solution having a concentration of 1 mg/mL. 100 mL of the peptide diluted in a carbonate buffer to a concentration of 10 mg/mL was added to Nunc MaxiSorp 96-well plate (Thermo Fisher Scientific) and was left at rest at 4° C. overnight for immobilization. The plate was washed with PBS-T twice, and 200 mL of 1%/BSA/PBS-T was added. The plate was left at rest at room temperature for 1 hour for blocking. The plate was washed with PBS-T twice, and 100 mL of the HRP-labeled antibody diluted in 1% BSA/PBS-T to a concentration of 100 ng/mL was added, followed by incubation at room temperature for 1 hour. The plate was washed with PBS-T four times, and 100 mL of TMB Soluble Reagent (ScyTek Laboratories) was then added for color development. 100 mL of TMB Stop Buffer (ScyTek Laboratories) was further added to terminate the reaction. Finally, using the Ensight plate reader (PerkinElmer), the wavelength at 450 nm was measured.

FIG. 1 shows the structures of the mRNA and protein of the CADM1 splice variant v8/9. (A) The CADM1 gene consists of 12 exons, and there are three main splice variants, namely, v(−) expressing in the brain, v8 expressing in the epithelium, and v8/9 expressing in the testis and SCLC. Exon 9 is comprised only in CADM1 v8/9. (B) The amino acid sequence specific to CADM1 v8/9 is present outside and just adjacent to the cell membrane and is released by being cleaved with ADAM17. The periphery of this site is rich in threonine residues and undergoes O-glycosylation. Ig-V and Ig-C2 indicate immunoglobulin-like loop structures.

<Results>

FIG. 2 shows the detection results of the CADM1 v9 fragment in a cell culture supernatant. (A) The total amount of CADM1 fragment or other cells and (B) the amount of the CADM1 v9 fragment, secreted in the culture supernatant of SCLC were measured according to a sandwich ELISA method. As a capture antibody, the anti-CADM1 mouse monoclonal antibody E9935 was used. As detection antibodies, the anti-CADM1 antibody E9919 and the anti-CADM1 v8/9 antibody F1222, which were HRP-labeled, were used. SBC5 cells not expressing CADM1, in which CADM1 v8 (epithelium type) or CADM1 v8/9 (SCLC/testis type) were stably expressed, were produced individually. As a result, in the CADM1 v8/9-expressing cells, secretion of the CADM1 v9 fragment was observed in the culture supernatant. In addition, almost no CADM1 v9 fragments were detected in the culture supernatants of human embryonic kidney cell-derived 293FT and adult T cell leukemia-derived ATN-1, which intrinsically express CADM1 v8, whereas the CADM1 v9 fragment was detected in the culture supernatants of NCI-H69 and NCI-H446 cells that are SCLC cells. Therefore, since the CADM1 v9 fragment was detected only in the culture supernatant of the cells expressing CADM1 v8/9, it was demonstrated that CADM1 v8/9 is certainly cleaved and a fragment is released, and also that the specificity of sandwich ELISA for detecting the CADM1 v9 fragment is high.

Figure 3:
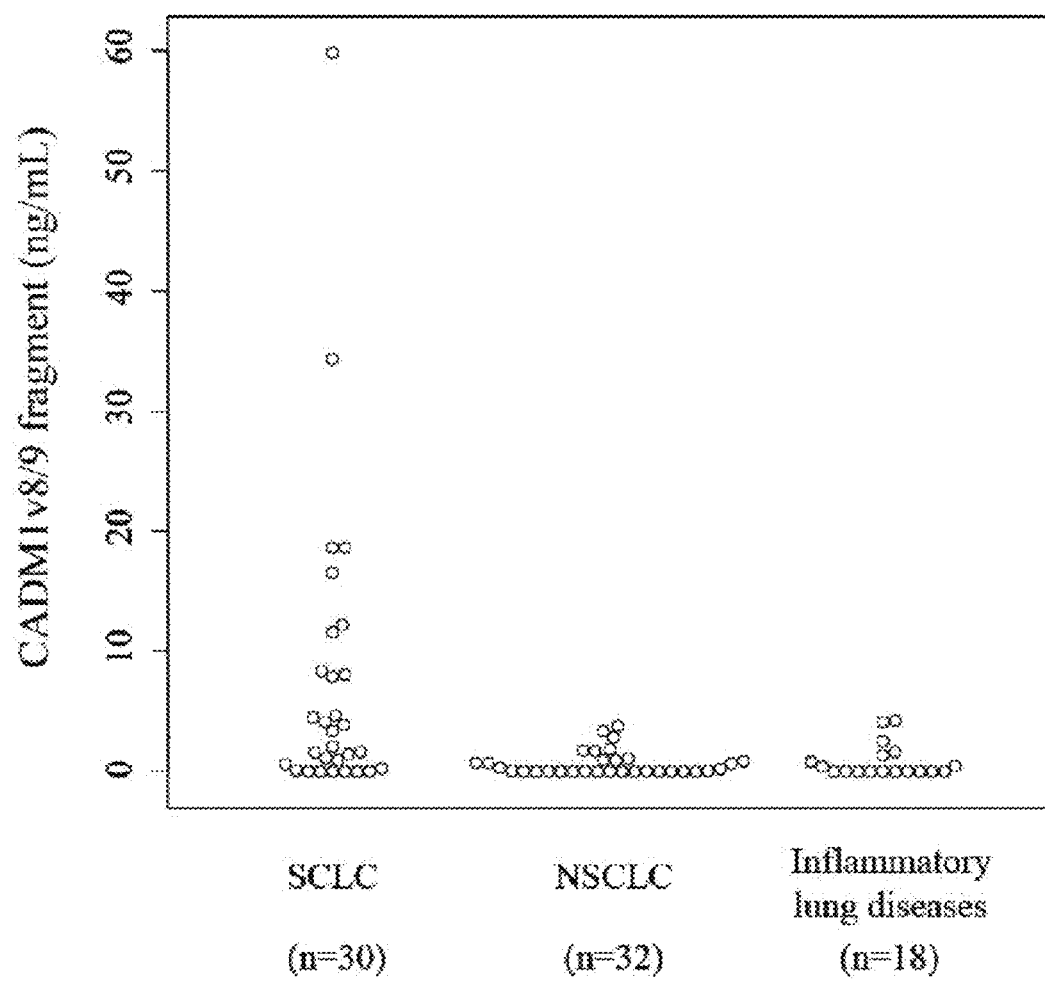
FIG. 3 shows the detection results of the v9 fragment of CADM1 in the serums of patients with lung cancer and inflammatory lung disease.

FIG. 3 shows the detection results of the CADM1 v9 fragment in the serums of patients with lung cancer and inflammatory lung disease. Using serum obtained by centrifuged blood sampled from the patients and removing cell components therefrom, detection of the CADM1 v8/9 fragment was carried out. Thirty (30) patients with small cell lung cancer (SCLC), 32 patients with non-small cell lung cancer (NSCLC) (20 patients with adenocarcinoma and 12 patients with squamous cell carcinoma), and 18 patients with inflammatory lung diseases were studied. As a result, the case of having a large amount of CADM1 v9 fragment was observed only in the SCLC patients. When the threshold is set at 3 ng/mL, the sensitivity was 47% (14/30) at a specificity of 92% (46/50), and thus, the usefulness of the CADM1 v9 fragment as a tumor marker was demonstrated.

The following table shows the detection rates of the CADM1 v9 fragment (SEQ ID NO: 27) in the serums of SCLC patients. When the threshold is set at 3 ng/mL, the cases positive for CADM1 v8/9 accounted for 47% (14/30) of the total SCLC cases, 3/12 (25%) of the limited stage cases (wherein the lesion is limited to ipsilateral thorax, contralateral mediastinum, and contralateral supraclavicular lymph node and does not have malignant pleural effusion and pericardial effusion), and for 10/13 (77%) of the extensive stage cases (wherein the lesion is not limited to ipsilateral thorax, contralateral mediastinum, and contralateral supraclavicular lymph node or has malignant pleural effusion or pericardial effusion). Hence, it was demonstrated that the CADM1 v9 fragment can be detected even in the limited-stage SCLC in a relatively early stage.

TABLE 1

| Classification | CADM1 v8/9 (+) |
| --- | --- |
| Limited stage | 3/12 (25%) |
| Extensive stage | 10/13 (77%) |
| Total | 14/30 (47%) |

Figure 4:
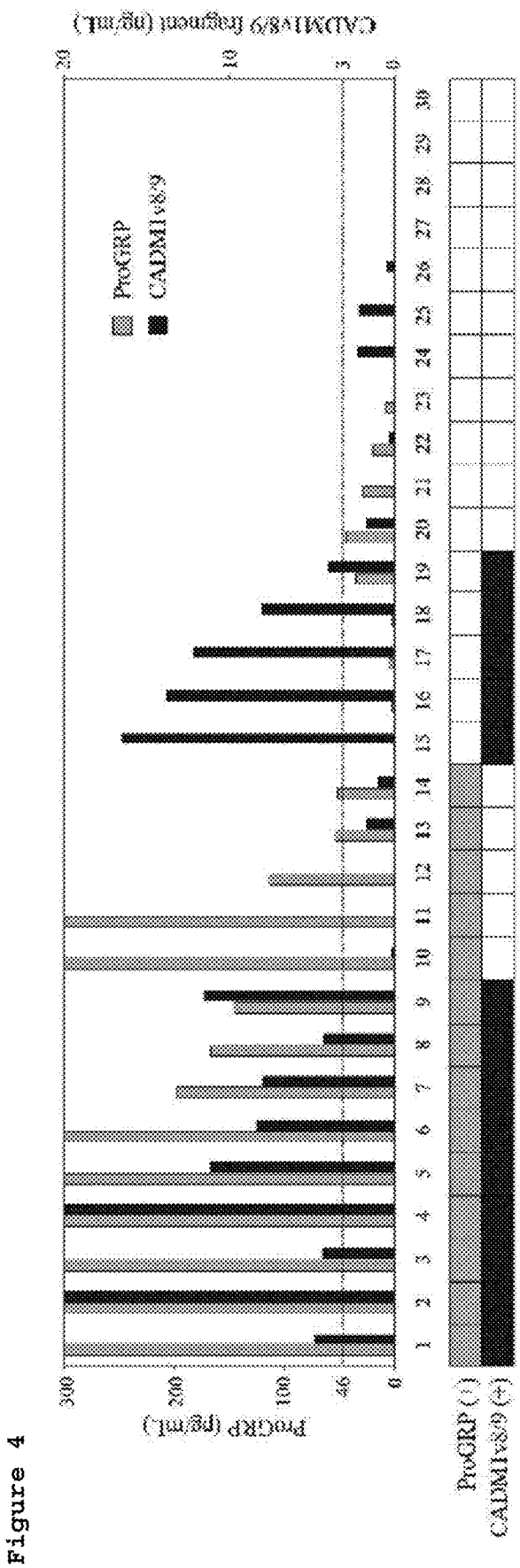
FIG. 4 shows a comparison between ProGRP and the v9 fragment of CADM1 in the serums of SCLC patients.

FIG. 4 shows a comparison between ProGRP and the CADM1 v9 fragment in the serums of SCLC patients. ProGRP was measured in 30 cases of SCLC patient serums, using Human Pro-Gastrin-releasing Peptide DuoSet Kit (R&D Systems), and the obtained value was compared with that of the CADM1 v9 fragment. When the threshold was set at 46 pg/mL, ProGRP was positive in 14 cases (47%). On the other hand, when the threshold was set at 3 ng/mL, the CADM1 v9 fragment was positive also in 14 cases (47%). There were observed 5 (17%) ProGRP-positive and CADM1 v8/9-negative cases and also 5 (17%) ProGRP-negative and CADM1 v8/9-positive cases. From these results, the improvement of the detection rate is expected by the combined use of ProGRP and the CADM1 v8/9 fragment as tumor markers. Besides, in the figure, a ProGRP value of 300 pg/mL or more and a CADM1 v8/9 fragment value of 20 ng/mL or more are not shown.

Figure 5:
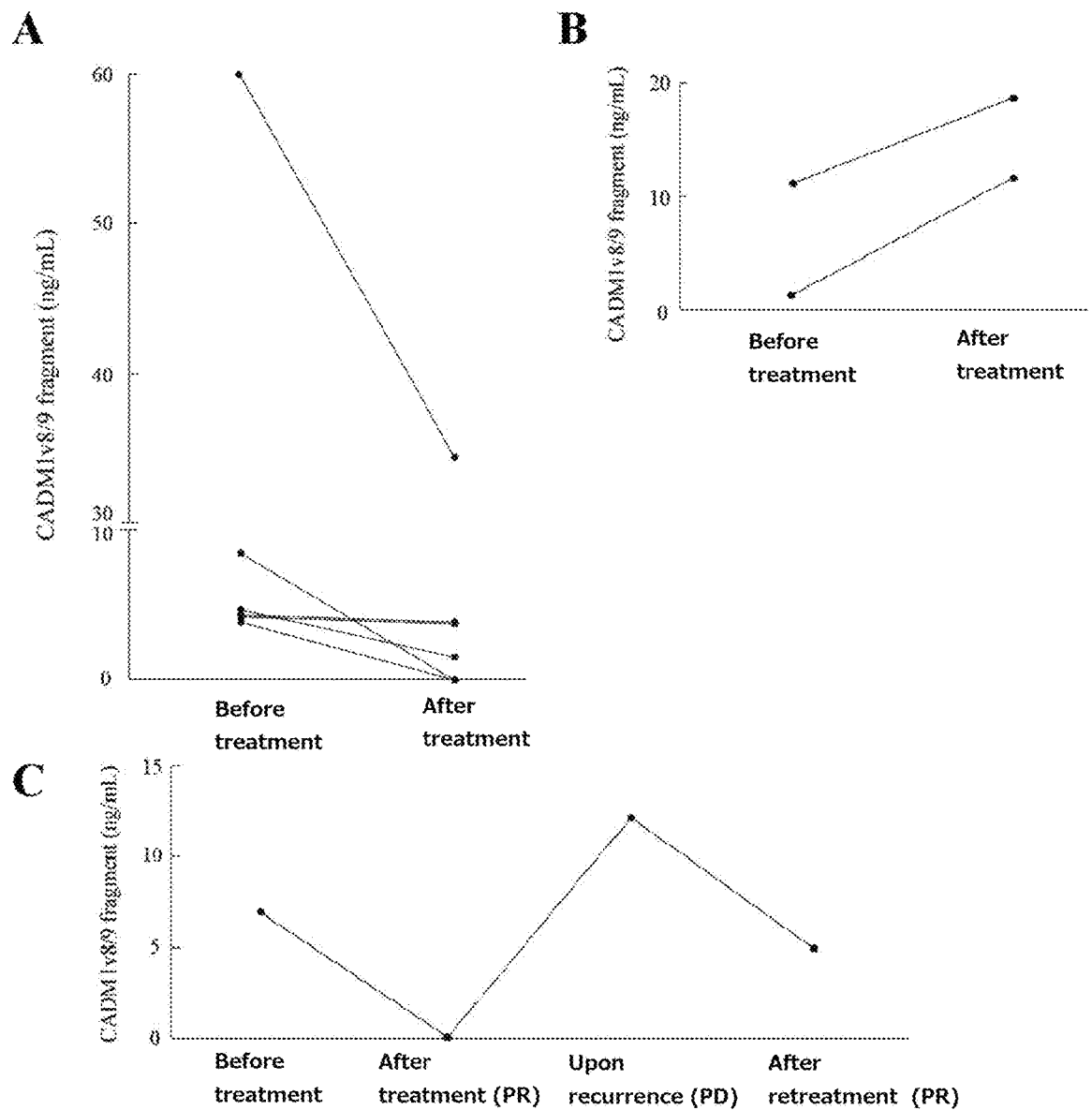
FIG. 5 shows a correlation between the therapeutic effect on SCLC and the amount of the v9 fragment of CADM1.

FIG. 5 shows a correlation between the therapeutic effect on SCLC and the amount of the CADM1 v9 fragment. With regard to SCLC cases for which blood was sampled multiple times before and after the treatment, the correlation between the therapeutic effects and the amount of the CADM1 v8/9 fragment was studied. (A) In 4 out of 6 cases that were determined to be Partial Response (PR; a state in which the size of the tumor was decreased by 30% or more), a significant reduction in the amount of the CADM1 v9 fragment was observed, and even in the remaining 2 cases, the amount of the CADM1 v9 fragment was slightly decreased. (B) In both of 2 cases that were determined to be Progressive Disease (PD; a state in which the size of the tumor was increased by 20% or more and 5 mm or more, or a novel lesion appeared), an increase in the amount of the CADM1 v9 fragment was observed. (C) In 1 case in which recurrence was found, when the state became PR as a result of the treatment, the amount of the CADM1 v9 fragment was decreased, and upon the recurrence, an increase in the amount of the CADM1 v9 fragment was observed. From these results, it was demonstrated that a change in the size of the tumor is correlated with the amount of the CADM1 v9 fragment in serum, and thus that the CADM1 v9 fragment is useful as a marker that reflects the state of a disease.

Figure 6:
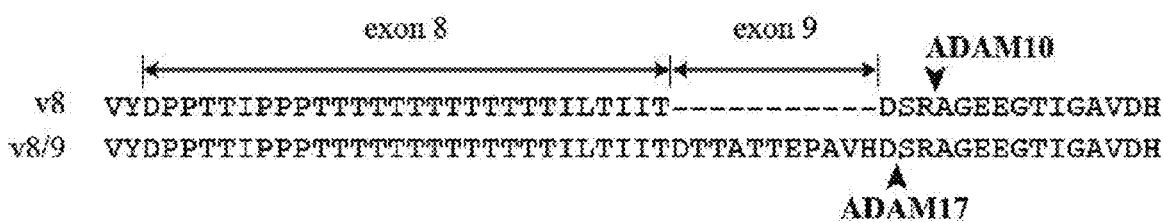
FIG. 6 shows the amino acid sequences encoded of CADM1 by exons 8 and 9, and the cleavage sites by protease. The top sequence is SEQ ID NO: 39 and the bottom sequence is SEQ ID NO: 40.

FIG. 6 shows the amino acid sequences encoded by exons 8 and 9 for CADM1, and the cleavage sites by protease. Some portions of the amino acids encoded by the splice variants v8 and v8/9 of CADM1 are shown in the figure. CADM1 v8 is cleaved by ADAM10, and CADM1 v8/9 is cleaved by ADAM17 (Nagara et al., Biochem Biophys Res Commun, 2012; Shirakabe et al., Sci Rep, 2017).

Figure 7:
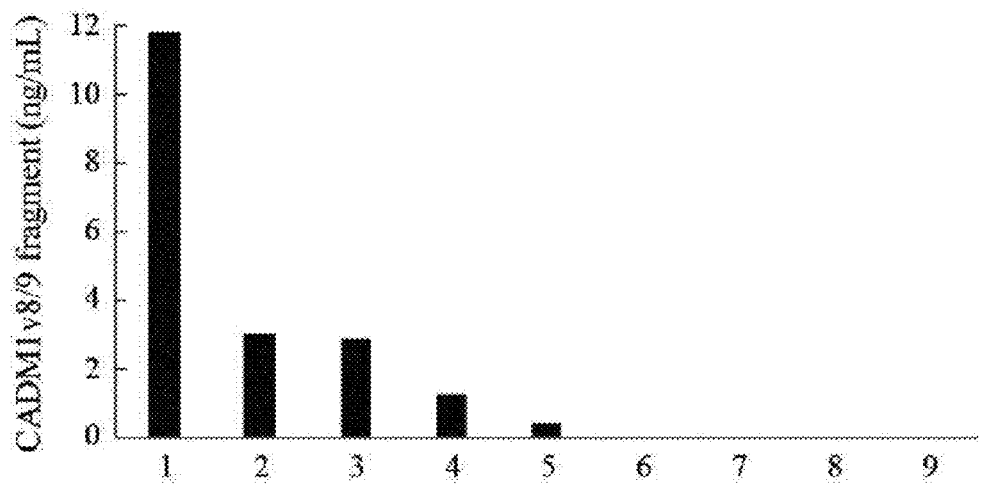
FIG. 7 shows the detection results of the v9 fragment of CADM1 in the pleural effusion of SCLC patients.

FIG. 7 shows the detection results of the CADM1 v9 fragment in the pleural effusion of SCLC patients. The amount of the CADM1 v9 fragment was measured in the pleural effusion sampled from 9 SCLC patients. As a result, there were cases where the amount of the CADM1 v9 fragment was high, as in the case of serum. These results demonstrate that the CADM1 v9 fragment derived from SCLC can be detected not only in blood but also in pleural effusion, and that the diagnosis can be carried out using such pleural effusion.

Figure 8:
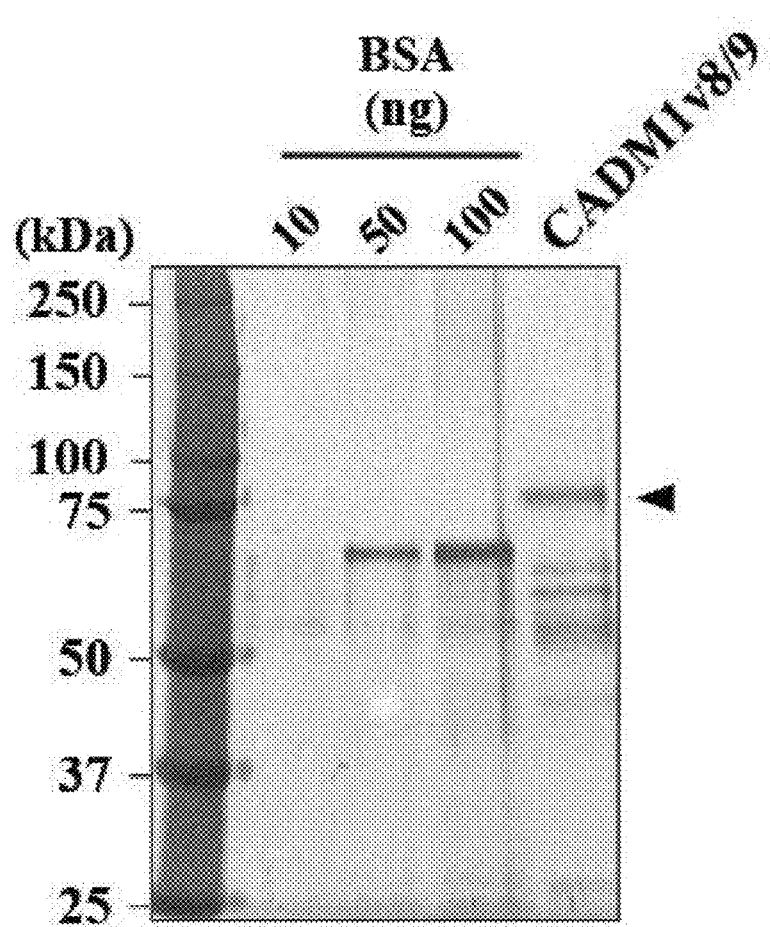
FIG. 8 shows the results of obtaining the purified protein of the v9 fragment of CADM1.

FIG. 8 shows the results of obtaining the purified protein of the CADM1 v9 fragment. A CADM1 v9 fragment was purified from the culture supernatant of the SBC5 cell line stably expressing CADM1 v8/9, using an anti-CADM1 antibody. The yield and purity of the purified protein were measured by silver staining after SDS-PAGE. The purified protein of the CADM1 v9 fragment was found in the position indicated with the arrowhead (approximately 80 kDa). BSA was used as a reference protein for concentration measurement.

Figure 9:
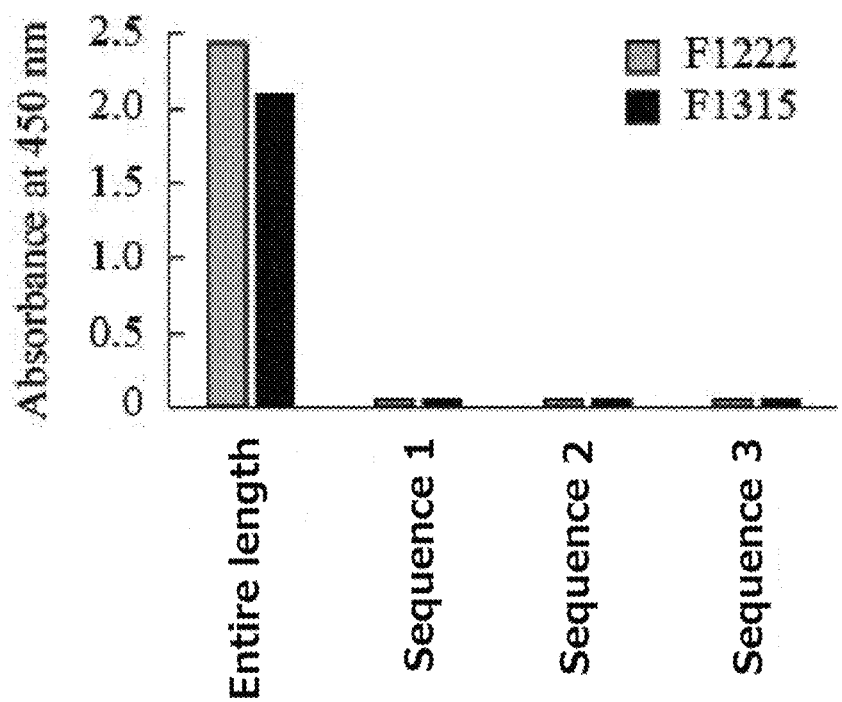
FIG. 9 shows the results of the narrowing-down of the epitope of the anti-CADM1 v9 antibody. The sequences from top to bottom are SEQ ID NO: 2, SEQ ID NO: 29, SEQ ID NO: 30, and SEQ ID NO: 31.

FIG. 9 shows the results of the narrowing-down of the epitope of the anti-CADM1 v9 antibody. In order to narrow down the epitope of the anti-CADM1 v9 antibody, a peptide consisting of 13 amino acids in entire length (SEQ ID NO: 2) used as an immunogen, and peptides obtained by dividing the aforementioned peptide into short fragments (SEQ ID NOS: 28 to 30) were synthesized, and the reactivity of these peptides to the anti-CADM1 v9 antibody was studied using an ELISA method. As a result, both of the antibodies F1222 and F1315 reacted with the entire-length peptide, but did not react with the divided peptides each consisting of 7 amino acids, and thus, it was demonstrated that the anti-CADM1 v9 antibody has an epitope that is longer than 7 amino acids.

Regarding the antibodies produced and used in the Examples, FIGS. 10 to 12 show the amino acid sequences and nucleotide sequences of the heavy chain and light chain of the antibody F1222, the amino acid sequences of the heavy chain and light chain of the antibody E9919, and the amino acid sequences of the heavy chain and light chain of the antibody E9935, respectively.

Sequence Listing Free Text

SEQ ID NO: 1 shows the amino acid sequence of CADM1 of exon 9.

SEQ ID NO: 2 shows the amino acid sequence of an antigen used in production of the antibody F1222 and the antibody F1315.

SEQ ID NO: 3 shows the amino acid sequence of heavy chain CDR1 of the antibody F1222.

SEQ ID NO: 4 shows the amino acid sequence of heavy chain CDR2 of the antibody F1222.

SEQ ID NO: 5 shows the amino acid sequence of heavy chain CDR3 of the antibody F1222.

SEQ ID NO: 6 shows the amino acid sequence of light chain CDR1 of the antibody F1222.

SEQ ID NO: 7 shows the amino acid sequence of light chain CDR2 of the antibody F1222.

SEQ ID NO: 8 shows the amino acid sequence of light chain CDR3 of the antibody F1222.

SEQ ID NO: 9 shows an amino acid sequence comprised in the heavy chain of the antibody F1222.

SEQ ID NO: 10 shows an amino acid sequence comprised in the light chain of the antibody F1222.

SEQ ID NO: 11 shows the amino acid sequence of heavy chain CDR1 of the antibody E9919.

SEQ ID NO: 12 shows the amino acid sequence of heavy chain CDR2 of the antibody E9919.

SEQ ID NO: 13 shows the amino acid sequence of heavy chain CDR3 of the antibody E9919.

SEQ ID NO: 14 shows the amino acid sequence of light chain CDR1 of the antibody E9919.

SEQ ID NO: 15 shows the amino acid sequence of light chain CDR2 of the antibody E9919.

SEQ ID NO: 16 shows the amino acid sequence of light chain CDR3 of the antibody E9919.

SEQ ID NO: 17 shows an amino acid sequence comprised in the heavy chain of the antibody E9919.

SEQ ID NO: 18 shows an amino acid sequence comprised in the light chain of the antibody E9919.

SEQ ID NO: 19 shows the amino acid sequence of heavy chain CDR1 of the antibody E9935.

SEQ ID NO: 20 shows the amino acid sequence of heavy chain CDR2 of the antibody E9935.

SEQ ID NO: 21 shows the amino acid sequence of heavy chain CDR3 of the antibody E9935.

SEQ ID NO: 22 shows the amino acid sequence of light chain CDR1 of the antibody E9935.

SEQ ID NO: 23 shows the amino acid sequence of light chain CDR2 of the antibody E9935.

SEQ ID NO: 24 shows the amino acid sequence of light chain CDR3 of the antibody E9935.

SEQ ID NO: 25 shows an amino acid sequence comprised in the heavy chain of the antibody E9935.

SEQ ID NO: 26 shows an amino acid sequence comprised in the light chain of the antibody E9935.

SEQ ID NO: 27 shows the amino acid sequence of a human CADM1 v9 fragment.

SEQ ID NO: 28 shows the amino acid sequence of a peptide consisting of 7 amino acids.

SEQ ID NO: 29 shows the amino acid sequence of a peptide consisting of 7 amino acids.

SEQ ID NO: 30 shows the amino acid sequence of a peptide consisting of 7 amino acids.

SEQ ID NO: 31 shows the nucleotide sequence of heavy chain CDR1 of the antibody F1222.

SEQ ID NO: 32 shows the nucleotide sequence of heavy chain CDR2 of the antibody F1222.

SEQ ID NO: 33 shows the nucleotide sequence of heavy chain CDR3 of the antibody F1222.

SEQ ID NO: 34 shows the nucleotide sequence of light chain CDR1 of the antibody F1222.

SEQ ID NO: 35 shows the nucleotide sequence of light chain CDR2 of the antibody F1222.

SEQ ID NO: 36 shows the nucleotide sequence of light chain CDR3 of the antibody F1222.

SEQ ID NO: 37 shows a nucleotide sequence comprised in the heavy chain of the antibody F1222.

SEQ ID NO: 38 shows a nucleotide sequence comprised in the light chain of the antibody F1222.

The invention claimed is:

1. An antibody that recognizes a v9 fragment of cell adhesion molecule 1 (CADM1), which comprises:
   (a)
   a heavy chain CDR1 consisting of an amino acid sequence as set forth in SEQ ID NO: 11,
   a heavy chain CDR2 consisting of an amino acid sequence as set forth in SEQ ID NO: 12,
   a heavy chain CDR3 consisting of an amino acid sequence as set forth in SEQ ID NO: 13,
   a light chain CDR1 consisting of an amino acid sequence as set forth in SEQ ID NO: 14,
   a light chain CDR2 consisting of an amino acid sequence as set forth in SEQ ID NO: 15, and
   a light chain CDR3 consisting of an amino acid sequence as set forth in SEQ ID NO: 16;
   (b)
   a heavy chain CDR1 consisting of an amino acid sequence as set forth in SEQ ID NO: 19,
   a heavy chain CDR2 consisting of an amino acid sequence as set forth in SEQ ID NO: 20,
   a heavy chain CDR3 consisting of an amino acid sequence as set forth in SEQ ID NO: 21,
   a light chain CDR1 consisting of an amino acid sequence as set forth in SEQ ID NO: 22,
   a light chain CDR2 consisting of an amino acid sequence as set forth in SEQ ID NO: 23, and
   a light chain CDR3 consisting of an amino acid sequence as set forth in SEQ ID NO: 24; or
   (c)
   a heavy chain CDR1 consisting of an amino acid sequence as set forth in SEQ ID NO: 3,
   a heavy chain CDR2 consisting of an amino acid sequence as set forth in SEQ ID NO: 4,
   a heavy chain CDR3 consisting of an amino acid sequence as set forth in SEQ ID NO: 5,
   a light chain CDR1 consisting of an amino acid sequence as set forth in SEQ ID NO: 6,
   a light chain CDR2 consisting of an amino acid sequence as set forth in SEQ ID NO: 7, and
   a light chain CDR3 consisting of an amino acid sequence as set forth in SEQ ID NO: 8.

2. The antibody according to claim 1, wherein the antibody comprises
   (a)
   a heavy chain having an amino acid sequence as set forth in SEQ ID NO: 17, and
   a light chain having an amino acid sequence as set forth in SEQ ID NO: 18;
   (b)
   a heavy chain having an amino acid sequence as set forth in SEQ ID NO: 9, and
   a light chain having an amino acid sequence as set forth in SEQ ID NO: 10; or
   (c)
   a heavy chain having an amino acid sequence as set forth in SEQ ID NO: 25, and
   a light chain having an amino acid sequence as set forth in SEQ ID NO: 26.

3. The antibody according to claim 1, wherein the v9 fragment of CADM1 is a v9 fragment of human CADM1.

4. The antibody according to claim 1, and further comprising a detectable label attached thereto.

5. A kit comprising the antibody according to claim 1 packaged together with a buffer, a container, or a reagent for performing an immunoassay.

6. The kit according to claim 5, wherein the antibody comprises a detectable label attached thereto.

7. The kit according to claim 5, wherein the immunoassay is an ELISA (Enzyme-Linked ImmunoSorbent Assay) method, a CLEIA (chemiluminescent enzyme immunoassay) method, a fluorescent antibody method, an enzyme antibody method, a Western blotting method, and an immunoprecipitation method.

8. A method of detecting a v9 fragment of CADM1 in a biological sample, which comprises contacting the antibody according to claim 1 with the biological sample and detecting bound antibody.

9. The method according to claim 8, wherein the biological sample is a serum sample, a plasma sample, or a pleural effusion sample.

10. The method according to claim 8, wherein the v9 fragment of CADM1 is expressed by a tumor cell.

11. The method according to claim 10, wherein the tumor cell is a small cell lung cancer cell.

12. A method of detecting a tumor that expresses v9 fragment of CADM1 in a subject, which comprises contacting the antibody according to claim 1 with a biological sample obtained from the subject and detecting bound antibody.

13. The method according to claim 12, wherein the biological sample is a serum sample, a plasma sample, or a pleural effusion sample.

14. The method according to claim 12, wherein the tumor is small cell lung cancer.

* * * * *

```
SEQUENCE LISTING

<160> NUMBER OF SEQ ID NOS: 40

<210> SEQ ID NO 1
<211> LENGTH: 11
<212> TYPE: PRT
<213> ORGANISM: Homo sapiens

<400> SEQUENCE: 1

Asp Thr Thr Ala Thr Thr Glu Pro Ala Val His
1               5                   10

<210> SEQ ID NO 2
<211> LENGTH: 13
<212> TYPE: PRT
<213> ORGANISM: Artificial
<220> FEATURE:
<223> OTHER INFORMATION: Antigen producing F1222 antibody

<400> SEQUENCE: 2

Cys Asp Thr Thr Ala Thr Thr Glu Pro Ala Val His Asp
1               5                   10

<210> SEQ ID NO 3
<211> LENGTH: 5
<212> TYPE: PRT
<213> ORGANISM: Mus musculus

<400> SEQUENCE: 3

Thr Tyr Ala Met Asn
1               5

<210> SEQ ID NO 4
<211> LENGTH: 19
<212> TYPE: PRT
<213> ORGANISM: Mus musculus

<400> SEQUENCE: 4

Arg Ile Arg Ser Lys Ser Asn Tyr Tyr Thr Thr Tyr Tyr Ala Asp Ser
1               5                   10                  15

Val Lys Asp

<210> SEQ ID NO 5
```

```
<211> LENGTH: 7
<212> TYPE: PRT
<213> ORGANISM: Mus musculus

<400> SEQUENCE: 5

Gln Arg His Gly Asn Phe Tyr
1               5

<210> SEQ ID NO 6
<211> LENGTH: 15
<212> TYPE: PRT
<213> ORGANISM: Mus musculus

<400> SEQUENCE: 6

Lys Ala Ser Gln Ser Val Asp Tyr Asp Gly Tyr Ser Tyr Met Asn
1               5                   10                  15

<210> SEQ ID NO 7
<211> LENGTH: 7
<212> TYPE: PRT
<213> ORGANISM: Mus musculus

<400> SEQUENCE: 7

Ala Ala Ser Asn Leu Glu Ser
1               5

<210> SEQ ID NO 8
<211> LENGTH: 9
<212> TYPE: PRT
<213> ORGANISM: Mus musculus

<400> SEQUENCE: 8

Gln Gln Ser Asn Glu Asp Pro Pro Thr
1               5

<210> SEQ ID NO 9
<211> LENGTH: 141
<212> TYPE: PRT
<213> ORGANISM: Mus musculus

<400> SEQUENCE: 9

Met Thr Leu Asn Met Leu Leu Gly Leu Lys Trp Val Phe Phe Val Val
1               5                   10                  15

Phe Tyr Gln Gly Val His Cys Glu Val Gln Leu Val Glu Ser Gly Gly
            20                  25                  30

Gly Leu Val Gln Pro Lys Gly Ser Leu Lys Leu Ser Cys Ala Ala Ser
        35                  40                  45

Gly Phe Thr Phe Asn Thr Tyr Ala Met Asn Trp Val Arg Gln Ala Pro
    50                  55                  60

Gly Lys Gly Leu Glu Trp Val Ala Arg Ile Arg Ser Lys Ser Asn Tyr
65                  70                  75                  80

Tyr Thr Thr Tyr Tyr Ala Asp Ser Val Lys Asp Arg Phe Thr Ile Ser
                85                  90                  95

Arg Asp Asp Ser Gln Ser Met Leu Tyr Leu Gln Met Asn Asn Leu Lys
            100                 105                 110

Thr Glu Asp Thr Ala Met Tyr Tyr Cys Ile Arg Gln Arg His Gly Asn
        115                 120                 125

Phe Tyr Trp Gly Gln Gly Thr Leu Val Thr Val Ser Ala
    130                 135                 140

<210> SEQ ID NO 10
```

```
<211> LENGTH: 131
<212> TYPE: PRT
<213> ORGANISM: Mus musculus

<400> SEQUENCE: 10

Met Glu Thr Asp Thr Ile Leu Leu Trp Val Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Lys Ala Ser Gln Ser
        35                  40                  45

Val Asp Tyr Asp Gly Tyr Ser Tyr Met Asn Trp Tyr Gln Gln Lys Pro
    50                  55                  60

Gly Gln Pro Pro Lys Leu Leu Ile Tyr Ala Ala Ser Asn Leu Glu Ser
65                  70                  75                  80

Gly Ile Pro Ala Arg Phe Ser Gly Ser Gly Ser Gly Thr Asp Phe Thr
                85                  90                  95

Leu Asn Ile His Pro Val Glu Glu Glu Asp Ala Ala Thr Tyr Tyr Cys
            100                 105                 110

Gln Gln Ser Asn Glu Asp Pro Pro Thr Phe Gly Ala Gly Thr Lys Leu
        115                 120                 125

Glu Leu Lys
        130

<210> SEQ ID NO 11
<211> LENGTH: 10
<212> TYPE: PRT
<213> ORGANISM: Mus musculus

<400> SEQUENCE: 11

Gly Phe Ser Ile Ile Ser Ser Ser Tyr Cys
1               5                   10

<210> SEQ ID NO 12
<211> LENGTH: 7
<212> TYPE: PRT
<213> ORGANISM: Mus musculus

<400> SEQUENCE: 12

Ile Cys Tyr Glu Gly Ser Ile
1               5

<210> SEQ ID NO 13
<211> LENGTH: 10
<212> TYPE: PRT
<213> ORGANISM: Mus musculus

<400> SEQUENCE: 13

Ser Arg Glu Arg Lys Ser Thr Met Asp Tyr
1               5                   10

<210> SEQ ID NO 14
<211> LENGTH: 6
<212> TYPE: PRT
<213> ORGANISM: Mus musculus

<400> SEQUENCE: 14

Gln Asp Ile Ser Asn Tyr
1               5

<210> SEQ ID NO 15
```

```
<211> LENGTH: 3
<212> TYPE: PRT
<213> ORGANISM: Mus musculus

<400> SEQUENCE: 15

Tyr Thr Ser
1

<210> SEQ ID NO 16
<211> LENGTH: 9
<212> TYPE: PRT
<213> ORGANISM: Mus musculus

<400> SEQUENCE: 16

Gln Gln Val Asn Ala Leu Pro Trp Thr
1               5

<210> SEQ ID NO 17
<211> LENGTH: 137
<212> TYPE: PRT
<213> ORGANISM: Mus musculus

<400> SEQUENCE: 17

Met Arg Leu Leu Gly Phe Leu Leu Cys Leu Ala Ala Leu Lys Ser
1               5                   10                  15

Val Leu Ser Gln Ile Gln Leu Lys Glu Ser Gly Pro Ala Val Ile Glu
            20                  25                  30

Pro Ser Gln Ser Leu Ser Leu Thr Cys Ile Val Ser Gly Phe Ser Ile
        35                  40                  45

Ile Ser Ser Ser Tyr Cys Trp His Trp Ile Arg Gln Pro Pro Gly Lys
    50                  55                  60

Gly Leu Glu Trp Met Gly Arg Ile Cys Tyr Glu Gly Ser Ile Tyr Tyr
65                  70                  75                  80

Ser Pro Ser Ile Lys Ser Arg Ser Thr Ile Ser Arg Asp Thr Ser Leu
                85                  90                  95

Asn Lys Phe Phe Ile Gln Leu Ser Ser Val Thr Asn Glu Asp Thr Ala
            100                 105                 110

Met Tyr Tyr Cys Ser Arg Glu Arg Lys Ser Thr Met Asp Tyr Trp Gly
        115                 120                 125

Gln Gly Thr Ser Val Thr Val Ser Ser
    130                 135

<210> SEQ ID NO 18
<211> LENGTH: 127
<212> TYPE: PRT
<213> ORGANISM: Mus musculus

<400> SEQUENCE: 18

Met Met Ser Ser Ala Gln Phe Leu Gly Leu Leu Leu Leu Cys Phe Gln
1               5                   10                  15

Gly Thr Arg Cys Asp Ile Gln Val Thr Gln Thr Thr Ser Ser Leu Ser
            20                  25                  30

Ala Ser Leu Gly Asp Arg Val Thr Ile Ser Cys Arg Ala Ser Gln Asp
        35                  40                  45

Ile Ser Asn Tyr Leu Asn Trp Tyr Gln Gln Lys Pro Asp Gly Thr Leu
    50                  55                  60

Lys Leu Leu Ile Tyr Tyr Thr Ser Arg Leu His Ser Gly Val Pro Ser
65                  70                  75                  80

Arg Phe Ser Gly Ser Gly Ser Gly Thr Asp Tyr Ser Leu Thr Ile Ser
```

```
                      85                  90                  95
Asn Leu Asp Gln Glu Asp Ile Ala Thr Tyr Phe Cys Gln Gln Val Asn
            100                 105                 110

Ala Leu Pro Trp Thr Phe Gly Gly Gly Thr Lys Leu Glu Ile Lys
            115                 120                 125

<210> SEQ ID NO 19
<211> LENGTH: 8
<212> TYPE: PRT
<213> ORGANISM: Mus musculus

<400> SEQUENCE: 19

Gly Tyr Thr Phe Thr His Tyr Trp
1               5

<210> SEQ ID NO 20
<211> LENGTH: 8
<212> TYPE: PRT
<213> ORGANISM: Mus musculus

<400> SEQUENCE: 20

Ile Asn Pro Gly Thr Gly Tyr Thr
1               5

<210> SEQ ID NO 21
<211> LENGTH: 16
<212> TYPE: PRT
<213> ORGANISM: Mus musculus

<400> SEQUENCE: 21

Ser Arg Ala Ser Tyr Tyr Ser Gly Ser Ser His Ala Trp Phe Gly Phe
1               5                   10                  15

<210> SEQ ID NO 22
<211> LENGTH: 10
<212> TYPE: PRT
<213> ORGANISM: Mus musculus

<400> SEQUENCE: 22

Gln Ser Val Asn Tyr Asp Gly Asp Asn Tyr
1               5                   10

<210> SEQ ID NO 23
<211> LENGTH: 3
<212> TYPE: PRT
<213> ORGANISM: Mus musculus

<400> SEQUENCE: 23

Ala Ala Ser
1

<210> SEQ ID NO 24
<211> LENGTH: 9
<212> TYPE: PRT
<213> ORGANISM: Mus musculus

<400> SEQUENCE: 24

Gln Gln Ser Tyr Glu Asp Pro Trp Thr
1               5

<210> SEQ ID NO 25
<211> LENGTH: 142
<212> TYPE: PRT
<213> ORGANISM: Mus musculus
```

<400> SEQUENCE: 25

Met Glu Arg His Trp Ile Phe Leu Phe Leu Phe Ser Val Thr Ala Gly
1               5                   10                  15

Val His Ser Gln Val Gln Leu Gln Gln Ser Gly Thr Glu Leu Ala Lys
            20                  25                  30

Pro Gly Ala Ser Val Lys Met Ser Cys Lys Ala Ser Gly Tyr Thr Phe
        35                  40                  45

Thr His Tyr Trp Met His Trp Val Lys Gln Arg Pro Gly Gln Gly Leu
    50                  55                  60

Glu Trp Ile Gly Phe Ile Asn Pro Gly Thr Gly Tyr Thr Glu Tyr Asn
65                  70                  75                  80

Gln Lys Phe Lys Asp Lys Ala Thr Leu Thr Ala Asp Lys Ser Ser Ser
                85                  90                  95

Thr Ala Tyr Ile Gln Leu Ser Ser Leu Thr Ser Glu Asp Ser Ala Val
            100                 105                 110

Tyr Tyr Cys Ser Arg Ala Ser Tyr Tyr Ser Gly Ser Ser His Ala Trp
        115                 120                 125

Phe Gly Phe Trp Gly Gln Gly Thr Leu Val Thr Val Ser Ala
    130                 135                 140

<210> SEQ ID NO 26
<211> LENGTH: 131
<212> TYPE: PRT
<213> ORGANISM: Mus musculus

<400> SEQUENCE: 26

Met Glu Thr Asp Thr Ile Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Lys Ala Ser Gln Ser
        35                  40                  45

Val Asn Tyr Asp Gly Asp Asn Tyr Met Asn Trp Tyr Gln Gln Lys Pro
    50                  55                  60

Gly Gln Pro Pro Lys Leu Leu Ile Tyr Ala Ala Ser Asn Leu Glu Ser
65                  70                  75                  80

Gly Ile Pro Ala Arg Phe Ser Gly Ser Gly Ser Gly Thr Asp Phe Thr
                85                  90                  95

Leu Asn Ile His Pro Val Glu Glu Glu Asp Ala Ala Thr Tyr Tyr Cys
            100                 105                 110

Gln Gln Ser Tyr Glu Asp Pro Trp Thr Phe Gly Gly Gly Thr Lys Leu
        115                 120                 125

Glu Ile Lys
    130

<210> SEQ ID NO 27
<211> LENGTH: 327
<212> TYPE: PRT
<213> ORGANISM: Homo sapiens

<400> SEQUENCE: 27

Gln Asn Leu Phe Thr Lys Asp Val Thr Val Ile Glu Gly Glu Val Ala
1               5                   10                  15

Thr Ile Ser Cys Gln Val Asn Lys Ser Asp Asp Ser Val Ile Gln Leu
            20                  25                  30

```
Leu Asn Pro Asn Arg Gln Thr Ile Tyr Phe Arg Asp Phe Arg Pro Leu
            35                  40                  45

Lys Asp Ser Arg Phe Gln Leu Leu Asn Phe Ser Ser Glu Leu Lys
 50                  55                  60

Val Ser Leu Thr Asn Val Ser Ile Ser Asp Glu Gly Arg Tyr Phe Cys
 65                  70                  75                  80

Gln Leu Tyr Thr Asp Pro Pro Gln Glu Ser Tyr Thr Ile Thr Val
                85                  90                  95

Leu Val Pro Pro Arg Asn Leu Met Ile Asp Ile Gln Lys Asp Thr Ala
                100                 105                 110

Val Glu Gly Glu Glu Ile Glu Val Asn Cys Thr Ala Met Ala Ser Lys
            115                 120                 125

Pro Ala Thr Thr Ile Arg Trp Phe Lys Gly Asn Thr Glu Leu Lys Gly
            130                 135                 140

Lys Ser Glu Val Glu Glu Trp Ser Asp Met Tyr Thr Val Thr Ser Gln
145                 150                 155                 160

Leu Met Leu Lys Val His Lys Glu Asp Asp Gly Val Pro Val Ile Cys
                165                 170                 175

Gln Val Glu His Pro Ala Val Thr Gly Asn Leu Gln Thr Gln Arg Tyr
            180                 185                 190

Leu Glu Val Gln Tyr Lys Pro Gln Val His Ile Gln Met Thr Tyr Pro
            195                 200                 205

Leu Gln Gly Leu Thr Arg Glu Gly Asp Ala Leu Glu Leu Thr Cys Glu
            210                 215                 220

Ala Ile Gly Lys Pro Gln Pro Val Met Val Thr Trp Val Arg Val Asp
225                 230                 235                 240

Asp Glu Met Pro Gln His Ala Val Leu Ser Gly Pro Asn Leu Phe Ile
                245                 250                 255

Asn Asn Leu Asn Lys Thr Asp Asn Gly Thr Tyr Arg Cys Glu Ala Ser
            260                 265                 270

Asn Ile Val Gly Lys Ala His Ser Asp Tyr Met Leu Tyr Val Tyr Asp
            275                 280                 285

Pro Pro Thr Thr Ile Pro Pro Pro Thr Thr Thr Thr Thr Thr Thr Thr
            290                 295                 300

Thr Thr Thr Thr Thr Ile Leu Thr Ile Ile Thr Asp Thr Thr Ala Thr
305                 310                 315                 320

Thr Glu Pro Ala Val His Asp
                325
```

```
<210> SEQ ID NO 28
<211> LENGTH: 7
<212> TYPE: PRT
<213> ORGANISM: Artificial
<220> FEATURE:
<223> OTHER INFORMATION: Peptides of 7 amino acids

<400> SEQUENCE: 28

Cys Asp Thr Thr Ala Thr Thr
 1               5
```

```
<210> SEQ ID NO 29
<211> LENGTH: 7
<212> TYPE: PRT
<213> ORGANISM: Artificial
<220> FEATURE:
<223> OTHER INFORMATION: Peptides of 7 amino acids

<400> SEQUENCE: 29
```

```
Thr Ala Thr Thr Glu Pro Ala
1               5
```

<210> SEQ ID NO 30
<211> LENGTH: 7
<212> TYPE: PRT
<213> ORGANISM: Artificial
<220> FEATURE:
<223> OTHER INFORMATION: Peptides of 7 amino acids

<400> SEQUENCE: 30

```
Thr Glu Pro Ala Val His Asp
1               5
```

<210> SEQ ID NO 31
<211> LENGTH: 15
<212> TYPE: DNA
<213> ORGANISM: Mus musculus

<400> SEQUENCE: 31
acctacgcca tgaac                                                        15

<210> SEQ ID NO 32
<211> LENGTH: 57
<212> TYPE: DNA
<213> ORGANISM: Mus musculus

<400> SEQUENCE: 32
cgcataagaa gtaaaagtaa ttattataca acatattatg ccgattcagt gaaagac         57

<210> SEQ ID NO 33
<211> LENGTH: 21
<212> TYPE: DNA
<213> ORGANISM: Mus musculus

<400> SEQUENCE: 33
cagaggcatg gtaacttcta c                                                 21

<210> SEQ ID NO 34
<211> LENGTH: 45
<212> TYPE: DNA
<213> ORGANISM: Mus musculus

<400> SEQUENCE: 34
aaggccagcc aaagtgttga ttatgatggt tatagttata tgaac                      45

<210> SEQ ID NO 35
<211> LENGTH: 21
<212> TYPE: DNA
<213> ORGANISM: Mus musculus

<400> SEQUENCE: 35
gctgcatcca atctagaatc t                                                 21

<210> SEQ ID NO 36
<211> LENGTH: 27
<212> TYPE: DNA
<213> ORGANISM: Mus musculus

<400> SEQUENCE: 36
cagcaaagta atgaggatcc tcccacg                                           27

<210> SEQ ID NO 37

<211> LENGTH: 423
<212> TYPE: DNA
<213> ORGANISM: Mus musculus

<400> SEQUENCE: 37

```
atgacattga acatgctgtt ggggctgaag tgggttttct ttgttgtttt ttatcaaggt      60
gtgcattgtg aggtgcagct tgttgagtct ggtggaggat tggtgcagcc taaagggtca     120
ttgaaactct catgtgcagc ctctggattc accttcaata cctacgccat gaactgggtc     180
cgccaggctc caggaaaggg tttggaatgg gttgctcgca taagaagtaa aagtaattat     240
tatacaacat attatgccga ttcagtgaaa gacaggttca ccatctccag agatgattca     300
caaagcatgc tctatctgca aatgaacaat ttgaagactg aggacacagc catgtattac     360
tgtatacgac agaggcatgg taacttctac tggggccaag ggactctggt cactgtctct     420
gca                                                                   423
```

<210> SEQ ID NO 38
<211> LENGTH: 393
<212> TYPE: DNA
<213> ORGANISM: Mus musculus

<400> SEQUENCE: 38

```
atggagacag acacaatcct gctatgggtg ctgctgctct gggttccagg ctccactggt      60
gacattgtgc tgacccaatc tccagcttct ttggctgtgt ctctagggca gagggccacc     120
atctcctgca aggccagcca agtgttgat tatgatggtt atagttatat gaactggtac     180
caacagaaac caggacagcc acccaaactc ctcatctatg ctgcatccaa tctagaatct     240
gggatcccag ccaggtttag tggcagtggg tctgggacag acttcaccct caacatccat     300
cctgtggagg aggaggatgc tgcaacctat tactgtcagc aaagtaatga ggatcctccc     360
acgttcggag ctgggaccaa gctggagctg aaa                                  393
```

<210> SEQ ID NO 39
<211> LENGTH: 45
<212> TYPE: PRT
<213> ORGANISM: Artificial Sequence
<220> FEATURE:
<223> OTHER INFORMATION: Amino acid sequence encoded of CADM1 by exons 8 and 9

<400> SEQUENCE: 39

```
Val Tyr Asp Pro Pro Thr Thr Ile Pro Pro Thr Thr Thr Thr Thr
1               5                   10                  15

Thr Thr Thr Thr Thr Thr Thr Thr Ile Leu Thr Ile Ile Thr Asp Ser
            20                  25                  30

Arg Ala Gly Glu Glu Gly Thr Ile Gly Ala Val Asp His
        35                  40                  45
```

<210> SEQ ID NO 40
<211> LENGTH: 56
<212> TYPE: PRT
<213> ORGANISM: Artificial Sequence
<220> FEATURE:
<223> OTHER INFORMATION: Amino acid sequence encoded of CADM1 by exons 8 and 9

<400> SEQUENCE: 40

```
Val Tyr Asp Pro Pro Thr Thr Ile Pro Pro Thr Thr Thr Thr
1               5                   10              15

Thr Thr Thr Thr Thr Thr Thr Thr Ile Leu Thr Ile Ile Thr Asp Thr
```

-continued

```
            20                  25                  30
Thr Ala Thr Thr Glu Pro Ala Val His Asp Ser Arg Ala Gly Glu Glu
        35                  40                  45

Gly Thr Ile Gly Ala Val Asp His
        50                  55
```